(12) United States Patent
Sastry et al.

(10) Patent No.: US 7,319,000 B1
(45) Date of Patent: Jan. 15, 2008

(54) COMPOSITIONS AND METHODS FOR ELICITING IMMUNE OR ANTI-INFECTIVE RESPONSES

(75) Inventors: Jagannadha K. Sastry, Houston, TX (US); Ralph B. Arlinghaus, Bellaire, TX (US); Chris D. Platsoucas, Houston, TX (US); Pramod N. Nehete, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 08/869,386

(22) Filed: Jun. 5, 1997

Related U.S. Application Data

(62) Division of application No. 07/945,865, filed on Sep. 16, 1992, now abandoned.

(51) Int. Cl.
*C12Q 1/70* (2006.01)
(52) U.S. Cl. .......................................... 435/5
(58) Field of Classification Search ............. 424/188.1, 424/184.1, 208.1, 204.1; 530/324, 325, 326
See application file for complete search history.

(56) References Cited

U.S. PATENT DOCUMENTS 5,013,548 A * 5/1991 Haynes et al.
5,019,387 A * 5/1991 Haynes et al. ........... 424/188.1
5,820,865 A * 10/1998 Berzofsky et al. ....... 424/188.1

OTHER PUBLICATIONS

Cohen, "Jitters Jeopardize AIDS Vaccine Trials" Science 262: 980-981, 1993.*
Butini, et al, "Comparative Analysis of HIV-Specific CTL Activity . . . " Abstract J306, J. Cellular Biochem Suppl. 18B, 1994.*
Fox, "No Winners Against AIDS", Bio/Technology vol. 12, p. 128, 1994.*
Takahashi, et al, "Structural Requirements for Class I MHC Molecule-Mediated . . . " J. Exp. Med. 170: 2023-2035, 1989.*
Yarchoan, et al. : Correlations between the in vitro . . . : J. Enz. Inh.: vol. 6: pp. 99-111, 1992.*
Gait, et al: Progress in an antiiHIV structure . . . : TIBTECH: vol. 13: pp. 430-438, Oct. 1995.*
Haynes et al.; Update on the issues of HIV vaccine development; Ann. Med; 28; pp. 39-41, 1996.*
Haynes et al.; Scientific and social issues of human immunodeficiency virus vaccine development; Science; vol. 260; pp. 1279-1286, May 1993.*
Koito, A., T. Hattori, T. Murakami, S. Matsushita, Y. Maeda, T. Yamamoto, and K. Takatsuki. 1989. A neutralizing epitope of human immunodeficiency virus type 1 has homologous amino acid sequences with the active site of inter-alpha-tripsin inhibitor. Int.*

* cited by examiner

*Primary Examiner*—Bruce R. Campell
*Assistant Examiner*—Emily M. Le
(74) *Attorney, Agent, or Firm*—Fulbright & Jaworski L.L.P.

(57) ABSTRACT

Disclosed are compositions and methods for the prevention and treatment of viral infections. The identification of distinct classes of peptides for use in both anti-viral vaccines and therapeutic formulations is reported. Peptide formulations are disclosed which enhance the systemic distribution, activity, and longevity of anti-viral cytotoxic T cells, and/or which protect human cells from HIV infection.

14 Claims, 12 Drawing Sheets

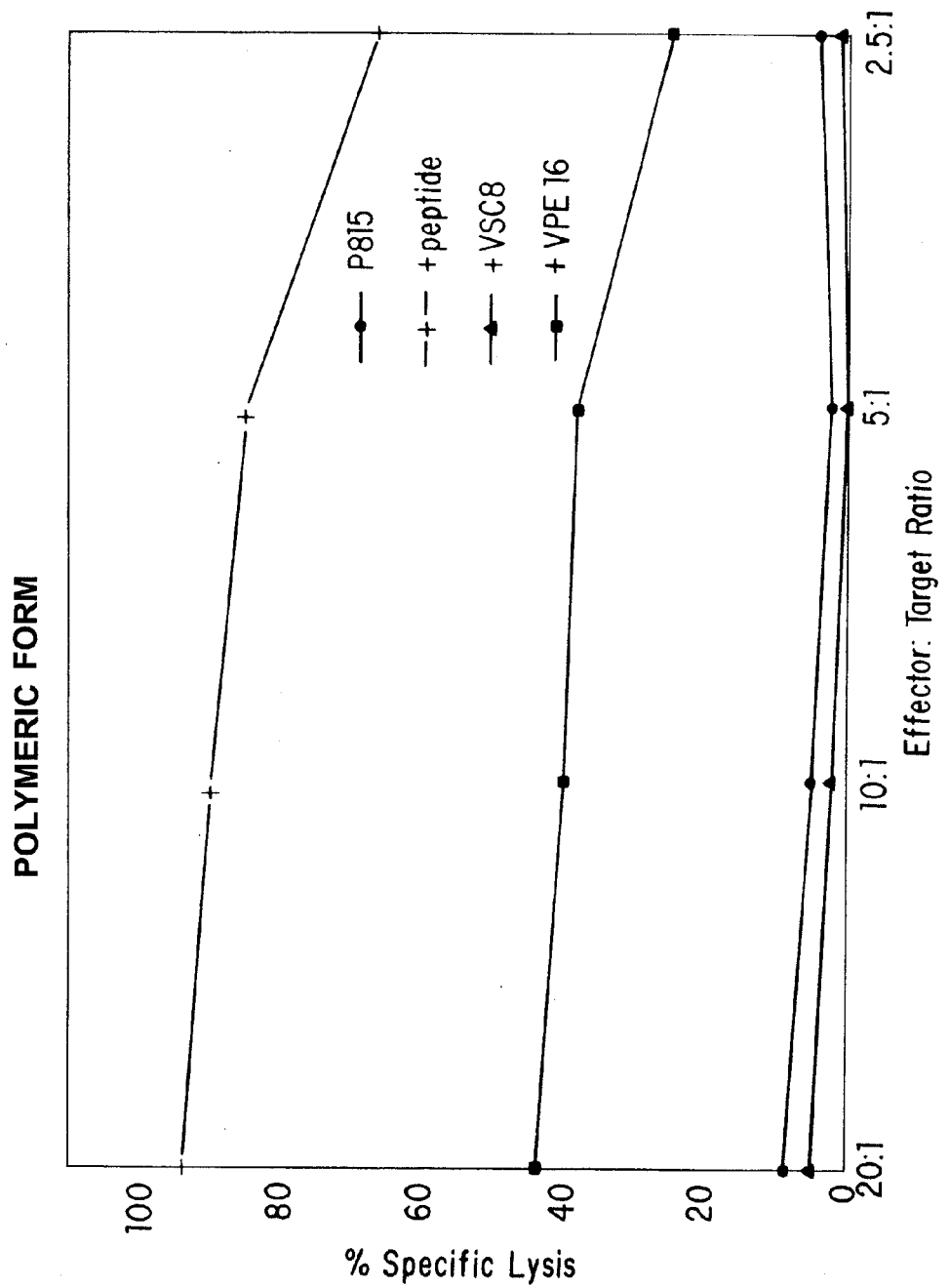

SEQUENCE LISTING (1) GENERAL INFORMATION:

(iii) NUMBER OF SEQUENCES: 46

```
(2) INFORMATION FOR SEQ ID NO:1:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:1:

Arg Ile Gln Arg Gly Pro Gly Arg Ala Phe Val Thr Ile Gly Lys
1               5                  10                  15

(2) INFORMATION FOR SEQ ID NO:2:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:2:

Cys Arg Ile Lys Gln Ile Ile Asn Met Trp Gln Gly Val Gly Lys Ala
1               5                  10                  15

Met Tyr Ala (2) INFORMATION FOR SEQ ID NO:3:

(i) SEQUENCE CHARACTERISTICS:
        (A) LENGTH: 24 amino acids
        (B) TYPE: amino acid
        (C) STRANDEDNESS:
        (D) TOPOLOGY: linear (xi) SEQUENCE DESCRIPTION: SEQ ID NO:3:

Asn Asn Thr Arg Lys Ser Glu Arg Ile Gln Arg Gly Pro Gly Arg Ala
1               5                  10                  15

Phe Val Thr Ile Gly Lys Ile Gly
            20

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:4:

Glu Gln Leu Trp Val Thr Val Tyr Tyr Gly Val Pro Val
1               5                  10

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:5:

Arg Ala Phe Val Thr Ile Gly Lys
1               5

(2) INFORMATION FOR SEQ ID NO:6:
```

-continued

```
        (i) SEQUENCE CHARACTERISTICS:
            (A) LENGTH: 13 amino acids
            (B) TYPE: amino acid
            (C) STRANDEDNESS:
            (D) TOPOLOGY: linear (xi) SEQUENCE DESCRIPTION: SEQ ID NO:6:

Thr Lys Gly Pro Gly Arg Val Ile Tyr Ala Thr Gly Gln
1               5                   10

(2) INFORMATION FOR SEQ ID NO:7:

(i) SEQUENCE CHARACTERISTICS:
            (A) LENGTH: 13 amino acids
            (B) TYPE: amino acid
            (C) STRANDEDNESS:
            (D) TOPOLOGY: linear (xi) SEQUENCE DESCRIPTION: SEQ ID NO:7:

His Ile Gly Pro Gly Arg Ala Phe Tyr Thr Thr Lys Asn
1               5                   10

(2) INFORMATION FOR SEQ ID NO:8:

(i) SEQUENCE CHARACTERISTICS:
            (A) LENGTH: 11 amino acids
            (B) TYPE: amino acid
            (C) STRANDEDNESS:
            (D) TOPOLOGY: linear (xi) SEQUENCE DESCRIPTION: SEQ ID NO:8:

Thr Tyr Gln Arg Thr Arg Ala Leu Val Thr Gly
1               5                   10

(2) INFORMATION FOR SEQ ID NO:9:

(i) SEQUENCE CHARACTERISTICS:
            (A) LENGTH: 16 amino acids
            (B) TYPE: amino acid
            (C) STRANDEDNESS:
            (D) TOPOLOGY: linear (xi) SEQUENCE DESCRIPTION: SEQ ID NO:9:

His Gly Glu Phe Ala Pro Gly Asn Tyr Phe Ala Leu Trp Ser Tyr Ala
1               5                   10                  15

(2) INFORMATION FOR SEQ ID NO:10:

(i) SEQUENCE CHARACTERISTICS:
            (A) LENGTH: 25 amino acids
            (B) TYPE: amino acid
            (C) STRANDEDNESS:
            (D) TOPOLOGY: linear (xi) SEQUENCE DESCRIPTION: SEQ ID NO:10:

Cys Thr Arg Pro Asn Asn Asn Thr Arg Lys Ser Ile Arg Ile Gln Arg
1               5                   10                  15

Gly Pro Gly Arg Ala Phe Val Thr Ile
            20                  25

(2) INFORMATION FOR SEQ ID NO:11:

(i) SEQUENCE CHARACTERISTICS:
            (A) LENGTH: 24 amino acids
            (B) TYPE: amino acid
            (C) STRANDEDNESS:
            (D) TOPOLOGY: linear
```

(xi) SEQUENCE DESCRIPTION: SEQ ID NO:11:

Tyr Asn Lys Arg Lys Arg Ile His Ile Gly Pro Gly Arg Ala Phe Tyr
1               5                   10                  15

Thr Thr Lys Asn Asn Ile Gly Cys
            20

(2) INFORMATION FOR SEQ ID NO:12:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:12:

Arg Ile His Ile Gly Pro Gly Arg Ala Phe Tyr Thr Thr Lys Asn
1               5                   10                  15

(2) INFORMATION FOR SEQ ID NO:13:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:13:

Ser Leu Ser Ile Gly Pro Gly Arg Ala Pro Arg Thr Arg Glu Ile
1               5                   10                  15

(2) INFORMATION FOR SEQ ID NO:14:

(i) SEQUENCE CHARACTERISTICS:
        (A) LENGTH: 24 amino acids
        (B) TYPE: amino acid
        (C) STRANDEDNESS:
        (D) TOPOLOGY: linear (xi) SEQUENCE DESCRIPTION: SEQ ID NO:14:

Asn Asn Thr Arg Lys Ser Ile Thr Lys Gly Pro Gly Arg Val Ile Tyr
1               5                   10                  15

Ala Thr Gly Gln Ile Ile Gly Asp
            20

(2) INFORMATION FOR SEQ ID NO:15:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:15:

Gly Ile Ala Ile Gly Pro Gly Arg Thr Leu Tyr Ala Arg Glu Lys
1               5                   10                  15

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:16:

Ser Ile Thr Lys Gly Pro Gly Arg Val Ile Tyr Ala Thr Gly Gln

```
1               5                  10                 15
```

(2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:17:

```
Arg Val Thr Leu Gly Pro Gly Arg Val Trp Tyr Thr Thr Gly Glu
1               5                  10                 15
```

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:18:

```
Ser Ile His Ile Gly Pro Gly Arg Ala Phe Tyr Ala Thr Gly Asp
1               5                  10                 15
```

(2) INFORMATION FOR SEQ ID NO:19:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:19:

```
Ser Ile Arg Ile Gly Pro Gly Lys Val Phe Thr Ala Lys Gly Gly
1               5                  10                 15
```

(2) INFORMATION FOR SEQ ID NO:20:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:20:

```
Ser Ile Tyr Ile Gly Pro Gly Arg Ala Phe His Thr Thr Gly Arg
1               5                  10                 15
```

(2) INFORMATION FOR SEQ ID NO:21:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:21:

```
Gly Ile His Phe Gly Pro Gly Gln Ala Leu Tyr Thr Thr Gly Ile
1               5                  10                 15
```

(2) INFORMATION FOR SEQ ID NO:22:

(i) SEQUENCE CHARACTERISTICS:
        (A) LENGTH: 15 amino acids
        (B) TYPE: amino acid
        (C) STRANDEDNESS:

(D) TOPOLOGY: linear (xi) SEQUENCE DESCRIPTION: SEQ ID NO:22:

Ser Ile Ser Ile Gly Pro Gly Arg Ala Phe Phe Ala Thr Thr Asp
1               5                   10                  15

(2) INFORMATION FOR SEQ ID NO:23:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:23:

Ser Thr Pro Ile Gly Leu Gly Gln Ala Leu Tyr Thr Thr Arg Gly
1               5                   10                  15

(2) INFORMATION FOR SEQ ID NO:24:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:24:

Ser Thr Pro Ile Gly Leu Gly Gln Ala Leu Tyr Thr Thr Arg Ile
1               5                   10                  15

(2) INFORMATION FOR SEQ ID NO:25:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:25:

Arg Thr Pro Thr Gly Leu Gly Gln Ser Leu Tyr Thr Thr Arg Ser
1               5                   10                  15

(2) INFORMATION FOR SEQ ID NO:26:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:26:

Arg Ile His Ile Gly Pro Gly Ala Arg Phe Leu Thr Thr Lys Asn
1               5                   10                  15

(2) INFORMATION FOR SEQ ID NO:27:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:27:

Arg Ile His Ile Gly Pro Gly Arg Ala Phe Phe Thr Thr Lys Asn
1               5                   10                  15

(2) INFORMATION FOR SEQ ID NO:28:

```
        (i) SEQUENCE CHARACTERISTICS:
            (A) LENGTH: 11 amino acids
            (B) TYPE: amino acid
            (C) STRANDEDNESS:
            (D) TOPOLOGY: linear (xi) SEQUENCE DESCRIPTION: SEQ ID NO:28:

Val Tyr Tyr Gly Val Pro Val Trp Lys Glu Ala
1               5                   10

(2) INFORMATION FOR SEQ ID NO:29:

(i) SEQUENCE CHARACTERISTICS:
            (A) LENGTH: 13 amino acids
            (B) TYPE: amino acid
            (C) STRANDEDNESS:
            (D) TOPOLOGY: linear (xi) SEQUENCE DESCRIPTION: SEQ ID NO:29:

Gly Val Pro Val Trp Lys Glu Ala Thr Thr Leu Phe Cys
1               5                   10

(2) INFORMATION FOR SEQ ID NO:30:

(i) SEQUENCE CHARACTERISTICS:
            (A) LENGTH: 11 amino acids
            (B) TYPE: amino acid
            (C) STRANDEDNESS:
            (D) TOPOLOGY: linear (xi) SEQUENCE DESCRIPTION: SEQ ID NO:30:

Ala His Lys Val Trp Ala Thr His Ala Cys Val
1               5                   10

(2) INFORMATION FOR SEQ ID NO:31:

(i) SEQUENCE CHARACTERISTICS:
            (A) LENGTH: 12 amino acids
            (B) TYPE: amino acid
            (C) STRANDEDNESS:
            (D) TOPOLOGY: linear (xi) SEQUENCE DESCRIPTION: SEQ ID NO:31:

Cys Val Pro Thr Asn Pro Val Pro Gln Glu Val Val
1               5                   10

(2) INFORMATION FOR SEQ ID NO:32:

(i) SEQUENCE CHARACTERISTICS:
            (A) LENGTH: 11 amino acids
            (B) TYPE: amino acid
            (C) STRANDEDNESS:
            (D) TOPOLOGY: linear (xi) SEQUENCE DESCRIPTION: SEQ ID NO:32:

Val Leu Glu Asn Val Thr Glu Asn Phe Asn Met
1               5                   10

(2) INFORMATION FOR SEQ ID NO:33:

(i) SEQUENCE CHARACTERISTICS:
            (A) LENGTH: 11 amino acids
            (B) TYPE: amino acid
            (C) STRANDEDNESS:
            (D) TOPOLOGY: linear (xi) SEQUENCE DESCRIPTION: SEQ ID NO:33:
```

```
Asn Asn Met Val Glu Gln Met His Glu Asp Ile
1               5                   10
```

(2) INFORMATION FOR SEQ ID NO:34:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:34:

```
Glu Gln Met His Glu Asp Ile Ile Ser Leu Trp Asp Gln
1               5                   10
```

(2) INFORMATION FOR SEQ ID NO:35:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:35:

```
Leu Trp Asp Gln Ser Leu Lys Pro Cys Val Lys Leu Thr
1               5                   10
```

(2) INFORMATION FOR SEQ ID NO:36:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:36:

```
Ser Leu Lys Pro Cys Val Lys Leu Thr Pro Leu Cys
1               5                   10
```

(2) INFORMATION FOR SEQ ID NO:37:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:37:

```
Ser Val Ile Thr Gln Ala Cys Ser Lys Val Ser Phe Glu
1               5                   10
```

(2) INFORMATION FOR SEQ ID NO:38:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:38:

```
Phe Glu Pro Ile Pro Ile His Tyr Cys Ala Phe Pro Gly Phe
1               5                   10
```

(2) INFORMATION FOR SEQ ID NO:39:

(i) SEQUENCE CHARACTERISTICS:
        (A) LENGTH: 11 amino acids
        (B) TYPE: amino acid

```
        (C) STRANDEDNESS:
        (D) TOPOLOGY: linear (xi) SEQUENCE DESCRIPTION: SEQ ID NO:39:

Lys Lys Phe Asn Gly Thr Gly Pro Cys Thr Asn
1               5                   10

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:40:

Gly Thr Gly Pro Cys Thr Asn Val Ser Thr Val Gln Cys
1               5                   10

(2) INFORMATION FOR SEQ ID NO:41:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:41:

Val Gln Cys Thr His Gly Ile Arg Pro Val Val Ser Thr Gln
1               5                   10

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:42:

Tyr Leu Arg Asp Gln Gln Leu Leu Gly Ile Trp Gly Cys
1               5                   10

(2) INFORMATION FOR SEQ ID NO:43:

(i) SEQUENCE CHARACTERISTICS:
        (A) LENGTH: 25 amino acids
        (B) TYPE: amino acid
        (C) STRANDEDNESS:
        (D) TOPOLOGY: linear (xi) SEQUENCE DESCRIPTION: SEQ ID NO:43:

Phe Leu Gly Phe Leu Gly Ala Ala Gly Ser Thr Met Gly Ala Ala Ser
1               5                   10                  15

Leu Thr Leu Thr Val Gln Ala Asn Gln
            20                  25

(2) INFORMATION FOR SEQ ID NO:44:

(i) SEQUENCE CHARACTERISTICS:
        (A) LENGTH: 28 amino acids
        (B) TYPE: amino acid
        (C) STRANDEDNESS:
        (D) TOPOLOGY: linear
```

```
    (xi) SEQUENCE DESCRIPTION: SEQ ID NO:44:

Cys Arg Ile Lys Gln Ile Ile Asn Met Trp Gln Gly Val Gly Lys Ala
1               5                   10                  15

Met Tyr Ala Pro Pro Ile Gly Gly Gln Ile Arg Cys
            20                  25

(2) INFORMATION FOR SEQ ID NO:45:

(i) SEQUENCE CHARACTERISTICS:
        (A) LENGTH: 36 amino acids
        (B) TYPE: amino acid
        (C) STRANDEDNESS:
        (D) TOPOLOGY: linear (xi) SEQUENCE DESCRIPTION: SEQ ID NO:45:

Cys Thr Arg Pro Asn Asn Asn Thr Arg Lys Ser Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35

(2) INFORMATION FOR SEQ ID NO:46:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO:46:

Lys Gln Ile Ile Asn Met Trp Gln Glu Val Gly Lys Ala Met Tyr Ala
1               5                   10                  15
```

COMPOSITIONS AND METHODS FOR ELICITING IMMUNE OR ANTI-INFECTIVE RESPONSES

This application is a division of U.S. Ser. No. 07/945,865, filed Sep. 16, 1992, now abandoned.

This invention was made with government support under grant AI-29308 awarded by the National Institutes of Health. The government has certain rights in the invention.

BACKGROUND OF THE INVENTION

1. Field of the Invention

The present invention relates generally to the prevention and treatment of viral infections. More particularly, this invention concerns the identification of distinct classes of peptides which may be advantageously combined for use in both anti-viral vaccines and therapeutic formulations. Peptide formulations are disclosed which enhance the systemic distribution, activity, and longevity of anti-viral cytotoxic T cells, and/or which protect human cells from HIV infection.

2. Description of the Related Art

AIDS was first recognized in the United States in 1981; the number of cases has been increasing at a dramatic pace since then. Since 1978 more than 2.4 million AIDS infections have been reported in the United States, alone (Rees, 1987). Once significant immunosuppressive symptoms appear in an infected individual, the expected outcome of the infection is death. There is currently no known treatment that can indefinitely delay or prevent the fatal consequences of the disease. Although the disease first manifested itself in homosexual or bisexual males and intravenous drug abusers, it has now spread to others by means such as intimate sexual contact with or receipt of blood products from a carrier of the virus.

The causative agent, associated with AIDS has been identified as a group of closely related retroviruses commonly known as Human T Cell Lymphotrophic Virus-type III (HTLV-III), Lymphadenopathy Viruses (LAV), AIDS-Related Viruses (ARV), or more recently named Human Immunodeficiency Virus (HIV). These viruses will be collectively referred to herein for convenience as HIV.

Like other retroviruses, HIV has RNA as its genetic material. When the virus enters the host cell, a viral enzyme known as reverse transcriptase copies the viral RNA into a double stranded DNA. The viral DNA migrates to the nucleus of the cell where it serves as a template for additional copies of viral RNA which can then be assembled into new viral particles. The viral RNA can also serve as messenger RNA (mRNA) for certain viral proteins, including the viral core proteins p18, p24, p13, and reverse transcriptase. RNA may also be "spliced" into specific viral mRNAs necessary to produce several other viral proteins including two glycosylated structural proteins known as gp41 and gp120 which are inserted in the outer membrane of the virus (Wain-Hobson et al., 1985). Purified gp120 is known to induce antibody in the goat, horse and rhesus monkey that neutralizes HIV in lab tests (Robey et al., 1986).

Vaccines have been used for many years to prevent infections caused by agents such as viruses. The general approach has been to inject healthy individuals with, for example, a killed or modified virus preparation in order to prime the individual's immune systems to mount an assault on the infecting virus. Recent advances in recombinant DNA technology have allowed safer methods of vaccination that involve use of exposed viral components produced by microbial systems. After sufficient purification, the viral component, for example a protein subunit, is administered as a vaccine in a suitable vehicle and/or an adjuvant. The latter stimulates the host's system in a way that improves the immune response to the viral subunit.

Another potential method of making a vaccine is by using chemically synthesized peptide fragments of a viral protein subunit. This method has several advantages over the other methods of producing vaccines, including purity of the product, reproducibility and specificity of the immune response.

Surface antigens of an infecting virus can elicit T cell and B cell responses. From the work of Milich and coworkers (Milich et al., 1986; Milich & McLachlan, 1986) it is clear that some regions of a protein's peptide chain can possess either T cell or B cell epitopes. These epitopes are frequently distinct from each other and can comprise different peptide sequences. Other examples include the work of Maizel et al., (1980) for hen eggwhite lysozyme, and Senyk et al., (1971) for glucagon. Thus, short stretches of a protein sequence can elicit a T cell response but not a B cell response. A more complete review of these and other observations pertinent to this point is included in the work of Livingstone & Fathman (1987).

A short peptide region within the surface protein of infectious Hepatitis B virus has been shown to elicit only a T cell response in mice (Milich et al., 1986). Specifically, a synthetic peptide, whose sequence is derived from amino acids numbered 120-132 located within the pre-S(2) domain of the Hepatitis B surface antigen gene, elicited a very strong T cell priming response to the peptide but stimulated only a very weak antibody response. In other words, mice mounted a poor antibody response to that peptide, but the T cells of immunized mice were efficiently primed (i.e. activated) to recognize that peptide as measured in T cell proliferation assays (Milich et al., 1986). The low level of the antibody produced by mice immunized with this peptide did not bind to the native viral surface antigen.

In contrast to the above-described results, a second peptide sequence (amino acids 132-145) elicited a very weak T-cell response in mice (Milich et al., 1986). This second peptide did, however, efficiently bind antibody raised against it under conditions where a T cell epitope is provided.

Mice were also immunized with a longer peptide made up of both of the above-mentioned T- and B-active peptide sequences. In this case, high titers of antibody were produced against the B site peptide but not the T site peptide. The combination of both T- and B-sites within one peptide should stimulate both T and B cell responses, as measured by producing a specific antibody to the B cell epitope of the peptide chain. Synthetic peptide antigens may be constructed to produce two types of immune responses: T-cell only and T cell combined with a B cell response.

Cellular immune responses provide a major mechanism for reducing the growth of virus-infected cells (Doherty et al., 1985). A report by Earl et al., (1986) demonstrated T-lymphocyte priming and protection against the Friend virus (a retrovirus)-induced mouse leukemia by a viral surface protein vaccine. Direct evidence for the role of a subset of T-lymphocytes (OKT8/LEU2 positive) in suppressing HIV growth in vitro has been obtained by Walker et al. (1986). This study further demonstrated that, after depletion of $CD8^+$ T-lymphocytes from the blood of HIV-infected individuals, large quantities of HIV were isolated from peripheral blood mononuclear cells of four of seven asymptomatic, seropositive homosexual men who were initially virus-negative or had very low levels of virus. Thus, the CD8+ cytotoxic T-lymphocytes (CTLs) may play a role in virus infected individuals to prevent HIV replication and disease progression.

The concept of identifying T-cell epitopes in proteins for inclusion in potential vaccine candidates has gained importance as a result of the demonstration by Townsend et al. (1986) that CTL epitopes of influenza nucleoprotein can be defined by short synthetic peptides. However, to date there are only three documented cases (Deres et al., 1989; Aichele et al., 1990; Kast et al., 1991) that describe the use of synthetic peptides in the in vivo priming of CTLs, these relate to influenza, Sendai and lymphocyte choriomeningitis viruses. In each of the above cases, the immunization protocols are cumbersome, require either modifications of peptides or many immunizations to be carried out to demonstrate CTLS, and do not lend themselves to the rapid screening of a large number of candidate substances. For example, the method of Aichele and colleagues (1990) involves three immunizations at one week intervals by the subcutaneous route, and takes four weeks before potential CTLs are obtained for assaying.

Candidate CTL epitopes in both structural and regulatory HIV proteins have been proposed (Takahashi et al., 1988; Nixon et al., 1988) but none of these have been shown to be capable of inducing virus-specific CTLs in vivo (Berzofsky, 1991). For example, although the peptide RIQRG-PGRAFVTIGK (R15K) SEQ ID NO:1 has been identified as a CTL epitope (Takahashi et al., 1988), in these studies the in vivo induction of R15K-specific CTLs was accomplished by infecting Balb/c mice with recombinant vaccinia virus expressing HIV env proteins (Takahashi et al., 1988) and attempts at immunization with free peptide have been unsuccessful (Berzofsky, J. A., 1991). Hart et al. (1991) were also unable to generate CTL responses on immunization with a single peptide having the CTL epitope sequence, CTRP-NNNTRKSIRIQRGPGRAFVTI (SEQ. ID ND:10).

The mechanisms underlying the induction of peptide-induced CTL responses in vivo are not yet fully understood. For instance, Gao et al (1991) reported that the addition of a T helper determinant to a CTL determinant, to create a hybrid peptide, did not enhance CTL generation against influenza virus. These results suggest that the induction of T helper cell activity is not specifically required for effective CTL generation, although the same studies showed that depletion of CD+ cells inhibited CTL generation in response to peptides.

Thus, there remains a need for both the development of techniques for the rapid identification of CTL epitopes that have the ability to induce a specific CTL response in vivo, and for the optimization of CTL induction. Previous assay methods for the identification of CTL-inducing epitopes that will function in vivo have suffered a number of drawbacks. The most notable of which are: the requirement for multiple injections of the material to be tested, a wait of up to 3 weeks or longer to determine whether the substance had a positive effect on CTL response, and the general need to include a modifier with the substance being tested in order to elicit a response. Clearly, a rapid method for the delineation of peptides with an in vivo CTL inducing capacity is of vital importance in the design of preventative and therapeutic strategies in relation to a wide variety of diseases.

The art currently also lacks an effective method of producing a systemic, long-lived and high level CTL response following peptide immunization. The development of a method to enhance the generation and systemic distribution of anti-viral CTL cells, in animals or humans, would be of great advantage in the development of vaccines against infectious viral agents. Not only would such a method be an important weapon for use against viruses, including AIDS and influenza, but it would also be applicable to vaccination against other agents such as parasites.

Although the gp120 V3 loop region is known to be essential for HIV-1 entry into cells (Travis et al., 1991; Freed & Riser, 1987; Freed et al., 1991), this knowledge has yet to lead to the development of an effective clinical strategy to prevent HIV infection. V3-derived synthetic peptides have been reported to inhibit syncytium formation between the HIV-1 infected cells, but only at concentrations of 100-300·M (Koito et al., 1989). In contrast, De Rossi et al. (1991) reported that V3-derived synthetic peptides actually enhanced HIV-1 infection of cells through a CD4-dependent mechanism. Therefore, in addition to the distinct lack of a suitable vaccine against HIV, there are also currently no effective means for arresting viral infection and for preventing disease progression in HIV-infected individuals.

SUMMARY OF THE INVENTION

The present invention addresses one or more of the foregoing or other disadvantages in the prior art by providing, firstly, compositions and methods for immunization against viral diseases, and secondly, therapeutic compositions and methods for use in inhibiting HIV infection. The improved immunization compositions, or vaccines, of the invention comprise synthetic peptide combinations which enhance the systemic distribution, level of activity, and longevity of virus-specific cytotoxic T cells (CTLs). The therapeutic formulations of the invention comprise synthetic peptides which function to protect human cells from HIV infection. The present invention therefore widely encompasses anti-viral, and particularly anti-HIV, compositions which have both preventative and therapeutic applications.

In important embodiments, the present invention concerns compositions and methods for enhancing the CTL response of an animal to a given immunogen, and particularly to a CTL-inducing peptide. A CTL-inducing peptide is a peptide, bearing a CTL-inducing epitope, which is capable of stimulating the formation, or increasing the activity, of specific cytotoxic T cells following its administration to an animal. The term "enhancing the CTL response", is used herein to encompass improvements in all aspects of the CTL response, such as for example, improving the systemic distribution, level of activity, and longevity of the response to CTL-inducing peptides.

The method of the present invention for enhancing a CTL response to an immunogen, such as a peptide, involves the addition of a composition including a separate and distinct class of peptides to the immunization mixture that possess T helper cell-inducing activity. To achieve enhancement of the CTL response in this manner one would therefore administer to the animal, in addition to the immunogen itself, an immunologically effective amount of a peptide bearing a T helper cell epitope.

In a related embodiment, the present invention provides a method of identifying a candidate substance capable of enhancing a CTL response. To identify such an enhancing substance, such as a peptide, one would administer to an animal both the candidate substance and an immunogen capable of inducing a CTL response. The CTLs would then be recovered from the animal and their activity, including systemic distribution and longevity, would be determined. A candidate substance capable of enhancing a CTL response would be identified as a substance that increased the CTL response, using any of the above parameters, over that observed in the presence of the immunogen alone.

The immunization methods of the present invention are generally applicable to enhancing CTL responses towards immunogens from any source, including those from a wide variety of infectious agents such as viruses or parasites. However, in preferred embodiments, the invention is exemplified by enhancing the CTL response against components of the HIV viral family. CTL responses may be generated against epitopes located within the products of any viral gene, such as, for example, the gag, pol, nef and env genes, with the products of the env genes being preferred targets.

Any one of a wide variety of peptide sequences may be employed as a CTL-inducing epitope in accordance with the present invention. These include the peptides listed in Table 1, which is, of course, an exemplary and not exhaustive list. In preferred embodiments, it is contemplated that peptides from the env (envelope) gene product, and more preferably, those derived from the V3 loop of HIV gp120, will be employed as CTL-inducing peptides. An exemplary list of V3 loop peptides from a variety of HIV-1 isolates is provided in Table 2 (SEQ ID NO:11 through SEQ ID NO:27, respectively, and SEQ ID NO:1). A specific example of a V3 loop-derived peptide found to be successful in generating CTL responses is the peptide R15K, having the sequence RIQRGPGRAFVTIGK (seq id no:1).

TABLE 2

SYNTHETIC PEPTIDES FROM THE V3 LOOP OF VARIOUS HIV-1 ISOLATES

| PEPTIDE NO. | STRAIN | SEQUENCE |
| --- | --- | --- |
| D23(24aa) | MN | YNKRKRIHIGPGRAFYTTKNNIGC |
| D24(15aa) | MN | RIHIGPGRAFYTTKN |
| D25(15aa) | WMJ-3 | SLSIGPGRAPRTREI |
| D26(24aa) | RF | NNTRKSITKGPGRVIYATGQIIGD |
| D27(15aa) | NY-5 | GIAIGPGRTLYAREK |
| D28(15aa) | RF | SITKGPGRVIYATGQ |
| D29(15aa) | CDC4 | RVTLGPGRVWYTTGE |
| D30(15aa) | SC | SIHIGPGRAFYATGD |
| D31(15aa) | Z3 | SIRIGPGKVFTAKGG |
| D32(15aa) | SF2 | SIYIGPGRAFHTTGR |
| D33(15aa) | MAL | GIHFGPGQALYTTGI |
| D34(15aa) | Z321 | SISIGPGRAFFATTD |
| D35(15aa) | Z6 | STPIGLGQALYTTRG |
| D37(15aa) | JY1 | STPIGLGQALYTTRI |
| D38(15aa) | ELI | RTPTGLGQSLYTTRS |
| D39(15aa) | MN(Y-L) | RIHIGPGARFLTTKN |
| D40(15aa) | MN(Y-F) | RIHIGPGRAFFTTKN |
| D44(15aa) (R15K) | IIIB | RIQRGPGRAFVTIGK |

The peptides of this table are represented by SEQ ID NOs:11-27 and SEQ ID NO:1, respectively.

Various methods are available to identify T helper cell-inducing epitopes suitable for use in accordance herewith. For example, the amphipathicity of a peptide sequence is known to effect its ability to function as a T helper cell inducer. In preferred embodiments, it is contemplated that one would wish to employ a T helper cell-inducing epitope having an amphipathicity value of from about plus 10 to

TABLE 1

CANDIDATE ANTI-HIV CTL-INDUCING EPITOPES

| GENE | PEPTIDE | | SOURCE OF CTLs | MHC/HLA | REFERENCE |
| --- | --- | --- | --- | --- | --- |
| gag | K25E | 18-42 | Human | Bw62 | Johnson et al., 1991 |
| | Q25E | 69-93 | Human | A2 | " |
| | V22F | 148-164 | Human | Bw57 | " |
| | N22A | 153-174 | Human | Bw57 | " |
| | S22H | 173-194 | Human | B14 | " |
| | G22R | 193-214 | Human | Bw52 | " |
| | N22V | 263-274 | Human | De | " |
| | Y19T | 262-280 | Mouse | H-2d | Michel et al., 1992 |
| | K22D | 263-284 | Human | Bw62 | " |
| | KL6C | 285-279 | Human | B27 | Nixon et al., 1988 |
| | R10K | 305-310 | Human | B14 | Johnson et al., 1991 |
| pol | 125E | 172-196 | Human | B8 | Walker et al., 1989 |
| | C17P | 205-219 | Mouse/Human | H-2k | Hosmalin et al., 1990 |
| | A25Q | 325-349 | Human | A11 | Walker et al., 1989 |
| | N26R | 348-366 | Human | A11 | " |
| | D25T | 359-383 | Human | Bw60 | " |
| | P25Y | 461-485 | Human | Bw60 | " |
| | E25G | 495-519 | Human | A11 | " |
| env | L22A | 25-46 | Human | A2 | Dadaglio et al., 1991 |
| | T20K | 196-212 | Human | A2 | " |
| | S171 | 295-311 | Human | A2 | " |
| | R15K | 315-329 | Mouse/Human | H-2d/A2 | Berzofsky et al., 1991 |
| | P7S | 374-380 | Human | A2 | Dadaglio et al., 1991 |
| | K12S | 381-392 | Human | A2 | " |
| | L20Y | 421-440 | Human | A2 | " |
| | Y | 101-610 | Human | A1 | " |
| | E9L | 584-592 | Human | B14 | Johnson et al., 1992 |
| | Y8L | 586-593 | Human | B8 | " |
| nef | Q25L | 73-97 | Human | A3.1 | Koenig et al., 1990 |
| | W10T | 110-120 | Human | B17B37 | Culmann et al., 1989 |
| | D16A | 176-191 | Mouse | H-2d | Michel et al., 1992 |
| | E17L | 184-199 | Mouse | H-2d | " | about plus 20. Other quantifiable characteristics include, for example, having an alpha helix turn of 100·15 degrees, or a 3₁₀ helix turn with 120·15 degrees. In embodiments relating specifically to HIV, T helper cell-inducing peptides including sequences derived from an HIV gp120 sequence which have an amphipathicity value within the above range will be preferred.

Again in relation to HIV, the use of peptides containing the sequence CRIKQIINMWQGVGKAMYA (C19A, seq id no:2) is preferred as this peptide was found to be particularly effective at enhancing CTL responses. However, peptides including other T helper cell-inducing epitopes may be employed. A full discussion of T helper cell-inducing epitopes is given in U.S. Pat. No. 5,128,319, incorporated herein by reference.

Related embodiments of this invention concern compositions for effecting improved CTL responses. Such compositions will generally include at least two peptides, the first of which will contain the CTL-inducing epitope against which the immune response is specifically desired, and second of which will comprise a T helper cell-inducing epitope. Naturally, a combination of such a composition in which the peptides are dispersed in a pharmacologically acceptable vehicle would be an ideal formulation for use as a vaccine.

The present invention further relates to the identification of synthetic peptides which protect human cells from HIV-1 infection. Such inhibitory peptides may be employed to inhibit HIV infection of cells, for use, for example, in assay protocols and as therapeutic agents for use in the treatment of AIDS.

As used herein, the term "HIV infection-inhibiting sequence" refers to a peptide sequence which prevents entry of the HIV virus into its target cell. As such, an inhibitory peptide may be characterized as including a peptide sequence that is involved in the infection process, or that functions to contact the target cell. Infection-inhibiting peptides particularly include peptides that comprise a sequence wherein antibodies against that sequence are capable of inhibiting HIV cellular infection.

The present invention discloses that synthetic peptides with sequences derived from the HIV-1 env gene product, gp120, have the capacity to inhibit HIV cellular infection. In particular, the inventors have identified HIV infection-inhibiting sequences within the V3 loop and at the N-terminal regions of gp120. It is also contemplated that HIV infection-inhibiting sequences may prove to be located within the CD4 binding region.

In preferred embodiments, the inventors contemplate the use of HIV infection-inhibiting peptides with sequences derived from the gp120 V3 loop. As detailed herein, peptides found to be of use in this regard include, for example, those peptides of Table 11, and particularly, peptides D23 (SEQ ID NO:11), D24 (SEQ ID NO:12), D25 (SEQ ID NO:13), D26 (SEQ ID NO:14), D30 (SEQ ID NO:18), D35 (SEQ ID NO:23), D38 (SEQ ID NO:25), D39 (SEQ ID NO:26), D40 (SEQ ID NO:27) and D44 (R15K, SEQ ID NO:1) the sequences of which are shown in Table 11A. These peptides have sequences derived from the V3 loops of a variety of strains such as mn, rf, wmj-3, sc, z6, eli, mn (y-1) and mn (y-p). Preferred V3-derived infection-inhibiting peptides are contemplated to include those listed in Table 11A, and those such as R15K, having the sequence RIQRGPGRAFVTIGK (seq id no:1), and also N24G, having the sequence NNTRK-SIRIQRGPGRAFVTIGKIG (seq id no:3).

An important aspect of the present invention is the discovery that peptides with sequences that correspond to sequences from a variety of different HIV isolates have the ability to inhibit HIV infection of cells. Further to those shown in Table 11A, these peptides include, for example, H13N (HIGPGRAFYTTKN, seq id no:7), a V3-loop peptide from HIV-1mn strain, and T13Q (TKGPGRVIYATGQ, seq id no:6), a V3-loop peptide from HIV-1rf strain. However, in regard to Table 11, it is important to note that this data was compiled from assays specifically directed to inhibiting infection by one HIV strain, namely HIV-1 IIIB. Therefore peptides such as D27 (SEQ ID NO:15), D28 (SEQ ID NO:16), D29 (SEQ ID NO:17), D31 (SEQ ID NO:19), D32 (SEQ ID NO:20), D33 (SEQ ID NO:21), D34 (SEQ ID NO:22) and D37 (SEQ ID NO:24), listed Table 11B, which may not show activity in one specific inhibitory assay may still have utility in preventing the infection of target cells by a variety of other HIV strains, for example against HIV strains ny-5, rf, cdc4, z3, sf2, ma1, z321 and jy1.

The inventors have also identified peptides from the gp120 N-terminus, such as E13V, having the sequence EQLWVTVYYGVPV (seq id no:4), as infection-inhibiting peptides. This is an important finding as this area of gp120 is known to be relatively conserved between different HIV strains.

It should also be noted that smaller peptides which include portions of these sequences, such as, for example, R8K, having the sequence RAFVTIGK (seq id no:5), have also been identified as having infection-inhibiting sequences. As such, smaller peptides and peptide fragments are considered to be useful in accordance herewith and to be within the scope of this invention.

The infection-inhibiting peptides of the present invention may include natural, or engineered, sequence variations and yet still function to prevent HIV entry into cells. As such, the biological functional equivalents of the peptides in Tables 1, 2 and 11, and peptides such as R15K (SEQ ID NO:1), N24G (SEQ ID NO:3), E13V (SEQ ID NO:4), H13N (SEQ ID NO:7) and T13Q (SEQ ID NO:6), are also considered to fall within the scope of the present invention.

Such biological functional peptide equivalents may include changes based upon hydropathic index of amino acids. It is believed that the relative hydropathic character of the amino acid determines the secondary structure of the resultant protein or peptide, which in turn defines its interaction with other molecules, such as for example, receptors, antibodies, and the like. It is generally known that certain amino acids may be substituted for other amino acids having a similar hydropathic index or score and still result in a peptide with similar biological activity (Kyte & Doolittle, 1982).

The hydropathic indices of the amino acids are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). Biological functional equivalents are considered to be those peptides which include the substitution of amino acids whose hydropathic indices are within ·2, and more preferably, within ·1, and even more preferably, within ·0.5.

Substitution of like amino acids can also be made on the basis of hydrophilicity, particularly where the biological functional equivalent protein or peptide thereby created is intended for use in immunological embodiments, as is the case for the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0·1); glutamate (+3.0·1); serine (+0.3); asparagine (+0.2); glutamine (+0.2); glycine (0); proline (−0.5·1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Similarly, biological functional equivalents are considered to be those peptides which include the substitution of amino acids whose hydrophilicity values are within ·2, and more preferably, within ·1, and even more preferably, within ·0.5.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the specific sequences described above, and their biological functional equivalents, other sequences may be employed as HIV infection-inhibiting peptides. For example, as mentioned above, it is contemplated that any sequence where anti-peptide antibodies against that sequence have been shown to inhibit viral entry into cells will be a suitable HIV infection-inhibiting peptide for use in accordance herewith. The advantages of the present invention include the demonstration that such peptides can function effectively at low concentrations, such as from between about 1·g/ml to about 1 ng/ml.

In any event, in light of the present disclosure, candidate sequences with the potential to function as HIV infection-inhibiting peptides can now be identified and tested. Such candidate peptides will likely include sequences located within the gp120 V3 loop or N-terminal region, or even within the CD4 binding region of gp120, and preferably, will be sequences against which antibodies have been raised and have been shown to inhibit or reduce HIV cellular infection. Candidate sequences may be synthesized as peptides and tested for the ability to inhibit HIV cellular infection.

As discussed above, in the compositions of the present invention, peptide(s) containing CTL-inducing epitope(s) may be combined with peptide(s) including T helper cell-inducing epitope(s) to create immunization, or vaccine, formulations. In regard to peptide cocktails for immunization, the use of peptides with sequences which correspond to the more conserved areas of HIV gp120 is generally preferred. Additionally, and specifically relating to HIV, the CTL-inducing peptide(s) may be combined with HIV infection-inhibiting sequence(s) as therapeutic formulations.

However, and importantly, compositions comprising all three of the distinct classes of peptide identified herein are also contemplated by the present invention. Such a single formulation would be capable of preventing infection of human cells by HIV-1 and of inducing HIV-1 specific CTL responses. Since all of these formulations are completely synthetic and defined, these reagents will be both economical and safe.

Naturally, any one of the peptides may have more than one immunological activity. This phenomenon is exemplified by the peptide R15K which has CTL-inducing and infection-inhibiting properties. In the most preferred embodiments, it is contemplated that peptides which do not induce the significant production of antibodies that bind to native HIV will be employed. In addition to being used directly as monomers, the peptides of the present invention may also be formulated as polymers or lipid-tailed peptides.

In further embodiments, the present invention concerns methods for assaying a composition for its ability to induce a cytotoxic T cell (CTL) response in an animal. Related to this, are methods for assaying a composition for its ability to enhance a CTL response induced by a distinct component. These screening methods include generally immunizing an animal, such as a human subject or an experimental animal such as a mouse, rat, rabbit, guinea pig, goat, rhesus monkey, or chimpanzee, thereafter collecting cells from lymph nodes or other lymphoid tissue from the animal, and then testing the tissue for the presence of CTLs that are primed to kill or lyse cells producing a component of an infectious agent, such as a viral envelope, core protein, one of the functional proteins (e.g., reverse transcriptase) or the like.

Thus, the method of the invention includes generally three steps, with the first step involving immunizing an animal with the composition to be tested. While it is believed that any accepted mode and route of immunization can be employed and nevertheless achieve some advantages in accordance herewith, the inventors have found particular advantages to be associated with intradermal immunization. Intradermal immunization is believed to be preferred because it serves to activate more efficiently the cell mediated arm of the immune system. Moreover, although where desired one may choose multiple injections of the immunizing substance, and even multiple sites of injection, the inventors have found that a particular advantage of the invention is that a single injection of the candidate will usually be sufficient to achieve detectable CTL activation in a nearby lymph node. Furthermore, although where desired one may employ immunization modifiers such as T-helper cell peptide sequences, lipid structures that induce micelle formation, peptide polymerization methods, or the like in association with the candidate composition, the inventors have found that the sensitivity of the assay is such that the use of such modifiers will generally not be required in order to achieve CTL priming.

Once immunization has been effected, it will then be necessary to recover cytotoxic T cells from lymphoid tissue of the immunized animal. The preferred lymphoid tissue will be lymph node tissue, and most preferably tissue from draining lymph nodes proximal to the site of injection. As used herein, the word "proximal node" is intended to refer to the node or nodes that are located proximal to the site of injection, e.g. the popliteal node of the mouse following foot pad injection. It is believed that the use of proximal or draining nodal tissue to identify CTL activation is one reason for the rapidity of the more preferred aspects of the invention. Such nodes are physically located in the proximity of the immunization site, or in the area draining the site of immunization, and also included are those draining nodes that are physically at a greater distance from the immunization site.

The final step of the assay in its most general sense involves determining whether said cytotoxic T cells have been activated by the composition. Although it is not generally required, it will typically be preferred to actually measure the level of activation, through, e.g., radioactive chromium-release assays, or other radioisotope assays, or single cell assays; also single cell cytotoxic assays using vital stains and/or cell-sorters could be employed.

Where measurement of activation of cytotoxic T cells is desired, a preferred method involves contacting a killing effective amount of said cytotoxic T cells with MHC-matched target cells that exhibit the candidate epitope on their cell surfaces; maintaining said contact for a time period sufficient for said cytotoxic T cells to lyse said target cells; and determining the degree of T cell-mediated lysis of said target cells. However, any method capable of detecting a specific CTL response may be employed, including but not limited to chromium-release assays, single-cell assays or even determination of cell-cell conjugates.

An advantage of the present invention is the speed with which one is able to determine the ability of the candidate substance to activate CTLs. Prior techniques have generally required a wait of a few weeks (Kast et al., 1991; Aichele et al., 1990). The present technique, though, typically requires only about 7 to 10 days following immunization. The reason for the reduced time necessary to achieve a CTL response with the assay of the present invention is believed to be the result of the route of immunization and the use of draining or proximal lymph node cells. A further advantage is the ability to test peptide candidates without the use of an associated modifier, such as carrier molecules, lipid tails, or T helper epitopes, to enhance its CTL activity.

Typically, the composition to be tested for CTL priming capability will comprise one or more peptides, or peptide multimers, believed to have or suspected of having useful activities. Through the application of the techniques of the present invention to such peptides, one will thus be enabled to determine whether such peptides do in fact have CTL priming activity. If so, then the peptide will be a candidate for inclusion in a CTL priming vaccine. It will be appreciated by those of skill in the art that while candidates for CTL priming activity will generally comprise peptides (or proteins), the use of the assay of the present invention in the context of non-peptidyl compounds is certainly not excluded.

It is proposed that the method of the present invention will find a broad range of application, particularly in the identification of components for use in the preparation of vaccines for the treatment and/or prevention of viral diseases such as AIDS, influenza, feline leukemia, bovine leukemia, Herpes virus infections, and even in the case of non-viral infectious diseases such as parasitic and bacterial infections. Therefore, in the case of embodiments directed to the identification of epitopes for promoting a specific anti-HIV CTL response, the invention will generally be concerned with the identification of peptides having the ability to direct a CTL response to HIV-infected cells.

In the context of vaccine development, the method will include first identifying a CTL-reactive composition in accordance with the foregoing method, and admixing the composition with one or more pharmaceutically acceptable diluents or additives, such as water, salts, emulsifiers and/or adjuvants. Of course, the amount of the composition added to the vaccine will vary depending on its ability to induce a specific CTL response, it solubility, and other biological responses. The selection of an appropriate amount of the identified CTL-priming composition will therefore be well within the skill of the art in light of the present disclosure.

In other embodiments, the invention involves a method of preparing cytotoxic T cells. In its most general sense, this method includes immunizing, preferably intradermally, an animal with a composition having the ability to induce a cytotoxic T cell response to a preselected epitope of a targeted protein. The epitope or epitopes employed may or may not be specific for CTL priming, and thus may or may not substantially induce antibodies that will cross react with the targeted protein. However, in the practice of this aspect of the invention, one will typically desire to recover cytotoxic T cells from lymph nodes of the animal for further use. Numerous potential uses of specifically primed CTLs are envisioned. For example, in the case of human therapy, it is contemplated that specifically primed CTLs may be cultured and administered to humans for the treatment of viral infections or patients with cancer. In this case, the CTLs are prepared by immunizing the species in vivo and isolating the immune cells to expand in vitro in the presence of appropriate peptide, cytokines and presenting cells.

Typically, for the induction of an HIV-directed CTL response, the invention will involve the use of peptides which comprise from 7 to about 30 amino acid residues, and have a sequence that corresponds to a domain of an HIV protein such as the gp16O envelope and core proteins, reverse transcriptase, tat, rev or other gene products expressed by the virus, which peptide includes within its structure a conserved region.

For the preparation of vaccines, peptide multimers are generally preferred in order to include multiple CTL epitopes within a single complex. Two specific classes of peptide multimers are disclosed. In one class, the amino-terminal residue of a peptide is peptide-bonded to a spacer peptide that contains an amino-terminal lysyl residue and one to about five amino acid residues such as glycyl residues to form a composite polypeptide. Those added residues of the spacer peptide do not interfere with the immunizing capacity of the multimer, nor with its capacity to form surfactant-like micelles in aqueous compositions. The alpha- and epsilon-amino groups of the amino-terminal lysyl residue are amidified with a $C_{12}$-$C_{18}$ fatty acid such as palmitic acid to form the reaction product that is used. The di-amide so formed forms surfactant-like micellular multimers in an aqueous composition.

A second class of multimer is a polymer having a peptide as a repeating unit. Here, each peptide is synthesized to contain a cysteine (Cys) residue at each of its amino- and carboxy-termini. The resulting di-cysteine-terminated (di-Cys) peptide is then oxidized to polymerize the di-Cys peptide monomers into a polymer or cyclic peptide multimers in which the peptide repeating units are linked by cystine (oxidized cysteine) residues.

A peptide multimer of either class can contain one or a plurality of different peptide sequences. A peptide of a multimer is an "active" peptide in that when used in a composition discussed below, the multimer can induce cell mediated immunity such as production of cytotoxic T cells. A multimer can also include an inactive peptide, for example to assist in dispersing the multimer in the aqueous medium. The lysyl-containing peptide spacer discussed before can be viewed as such an inactive peptide.

The peptide multimer is utilized in an aqueous composition (inoculum). That composition contains water having a before-described multimer dispersed therein. The composition, when used to immunize an immunocompetent host animal such as a mouse, has the capacity of inducing cell mediated immunity such as cytotoxic T cell activation to the native HIV protein corresponding in sequence to that of an active peptide of the multimer, but does not substantially induce production of antibodies that immunoreact with that corresponding native HIV protein. The composition thus contains an immunizing effective amount of a before-discussed multimeric peptide.

DETAILED DESCRIPTION OF THE PREFERRED EMBODIMENTS

Figure 1:
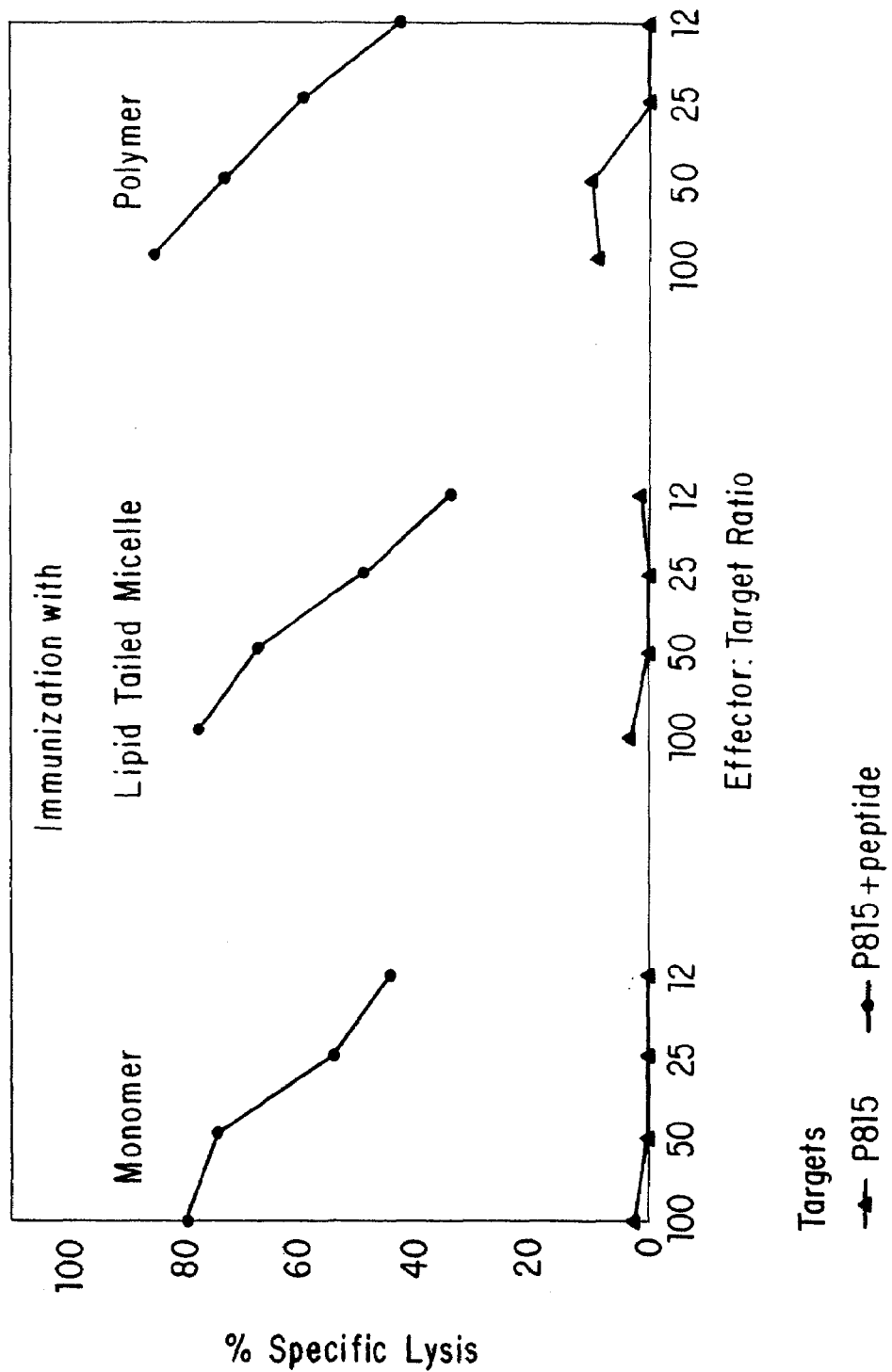
FIG. 1. CTL activity of popliteal lymph node (PLN) cells from Balb/c mice after immunization with HIV env V3-loop R15K peptide (aa 315-329, seq id no:1) in three forms. A, linear monomer; B, di-sulphide-linked polymers formed by cysteine residues added at both the N- and C-termini; C, lipid-tailed micelles formed by conjugation to a dipalmityl-lysine-glycine-glycine at the N-terminus (Hopp, 1984; Sastry et al., 1991). Balb/c mice (6-8 weeks of age) were immunized in the hind-foot pad with the peptide (100·g in a 1:1 emulsion with CFA). After 10 days, cells obtained from the PLN were re-stimulated in vitro for 5 days with irradiated (3300 rads) syngeneic mouse spleen cells that had been pre-treated with the monomeric form of the peptide (40·g/ml) for 2 h at 37·C. The cell mixtures were maintained in 5-10 ml of Click's medium (Click et al., 1972) supplemented with 10% fetal calf serum (FCS) and 50·M 2-mercaptoethanol, then washed three times with RPMI 1640 medium, 10% FCS. The CTL activity was determined by $^{51}$Cr-release assay (Platsoucas & Good, 1981) against syngeneic target cells (P815) with or without pre-treatment with the monomeric form of the peptide for 2 h at 37·C.

AIDS is a highly infectious and fatal disease caused by a group of closely related retroviruses commonly known as HIV. There are currently no vaccines to prevent HIV infection, and no effective therapeutic agents to arrest progression once infection has been initiated. The present invention addresses both of these current failings through the use of peptide technology in the development of formulations for anti-viral vaccination and treatment.

Initially, the present inventors developed a rapid method for the identification of peptides which have the ability to induce a specific CTL response in vivo. This method is broadly applicable to both screening and vaccination, and is relevant to the development of preventative vaccines, not only for AIDS, but also for a wide variety of other diseases. These methods of CTL induction were then refined, by the addition of T helper cell-inducing peptides, leading to particularly effective compositions and methods for producing systemic, long-lived and high level CTL activity in response to peptide immunization.

In addition to vaccine formulations, the inventors have also identified peptide sequences which function to effectively inhibit the entry of HIV into human target cells. It is envisioned that these peptides, which arrest viral infection, will form the basis of effective anti-HIV therapeutics which halt viral spread and disease progression in HIV-infected patients.

The use of peptides, for example, instead of proteins, in clinical embodiments is generally preferred for various reasons. These include the low cost and relative ease of large scale preparation, and the reliability of the product. Also their biological properties are preferable, such as the ease with which peptides can penetrate tissues, and their low immunogenicity. Prior to clinical use, peptides may be stabilized by the addition of groups to the N- or C-termini, for example, by acylation or amidation. The formulation of the peptides of the present invention into various polymers is discussed in detail below.

One aspect of the present invention is a novel and rapid method for screening candidate compounds, such as peptides or multimers thereof, to identify appropriate CTL-inducing active compounds for use, for example, in CTL vaccines. In preferred screening procedures, candidate peptides or peptide multimers are assayed for in vivo CTL-induction by injecting the test substance into an experimental animal, recovering T cells from the lymph nodes and measuring the activity (priming) of such CTLs. Most preferably immunization would involve a single intradermal injection of the test peptide in complete Freund's adjuvant (CFA) into an appropriate site, such as the hind-foot pad of a mouse, recovering lymph node T cells, preferably from the draining popliteal lymph nodes (PLN), and determining their CTL activity by assaying the T cell-mediated lysis of MHC-matched target cells decorated with the candidate peptide or expressing the parent protein. This procedure allows the results to be obtained only 8-10 days after immunization.

Employment of such a screening procedure will result in the identification of T cell active peptides, whether they be peptides that induce substantially only a CTL response, or also induce an antibody response (i.e., B cell reactive). A plurality of strains of mice that vary in their histocompatibility genes may be used for these screenings. Peptides that have a broad response in the various MHC genotypes should be selected for further study in primates, and finally humans. Exemplary assay procedures are found hereinafter.

The synthesis of peptides can be achieved using an automated peptide synthesizer. For example, peptides can be synthesized using the Merrifield solid phase method (Merrifield, 1963) either on a modified Vaga 250 automatic peptide synthesizer or by the "Bag" method, as described by Houghton et al. (1985). Following the synthetic reactions, the completed peptides are then recovered. In the above two methods this involves the removal of the T-BOC blocking groups and hydrolysis of the peptide from the resin using hydrofluoric acid (HF) treatment at 0·C for 1 hour. The various organic by-products can then be removed, for example by extraction with ether, and the peptides extracted from the supporting resin with a reagent such as 25% acetic acid.

In the rapid screening method for the identification of appropriate CTL-inducing candidate compounds, the inventors have found that the intradermal immunization of a mouse can be advantageously employed. Intradermal immunization is believed to be particularly effective as it serves to efficiently activate the cell mediated limb of the immune system. The inventors have found that even more advantageous aspects of this immunization protocol are (i) that a single injection of the candidate will usually be sufficient to achieve detectable CTL activation, and (ii) that the sensitivity of the assay is such that the use of immunization modifiers will generally not be required in order to achieve CTL priming.

Accordingly, in preferred screening embodiments, mice are immunized by intradermal injection into the hind footpad with an appropriate composition, such as 100·g of the test peptide in a 1:1 emulsion with complete freund's adjuvant (CFA). After a period of time sufficient to induce a CTL response, such as 10 days, the draining popliteal lymph nodes (PLN) are surgically removed and the cells were separated by mild homogenization. The PLN cells thus obtained, typically between 10-50×10$^6$ cells/lymph node/mouse, are maintained in 5-10 ml of a solution such as Click's medium, 10% FCS, 50·M 2-mercaptoethanol, and re-stimulated for 5 days, in vitro, with irradiated (3300 rads) syngeneic mouse spleen cells pre-treated with the candidate peptide. A syngeneic cell expressing the parent protein from which the peptide is derived, such as the HIV gp160 protein, would be an appropriate target cell. However, the inventors contemplate that peptide-decorated spleen cells which can be easily generated, for example by pre-treating the cells with the peptide monomer at a concentration of approximately 40·g/ml for 2 hours at 37·C, may be preferred for use in accordance with the present invention.

The re-stimulated effector cells are then washed, for example with RPMI 1640 medium, 10% FCS, resuspended at an appropriate cell density in the region of 5×10$^6$/ml, and assayed for CTL activity. A suitable method of assaying for CTL activity is to determine the release of a non-metabolizable radiolabeled substance from specific target cells which have been pre-loaded with the substance. Measuring the release of $^{51}$Cr from peptide-treated syngeneic cells, as described by Platsoucas & Good (1981), is considered by the inventors to be a particularly suitable method.

To generate peptide-expressing target cells for use in the CTL assay, appropriate syngeneic cells, such as P815 cells, are first loaded with radioactive compound such as chromium. This can be achieved by incubating the cells for 2 hours at 37·C with 25·Ci of $^{51}$Cr. The cells are then washed three times and incubated for an additional 2 hours at 37·C with the monomeric form of the test peptide at a concentration of approximately 40·g/ml. The cells are then washed twice with a solution such as RPMI medium, 10% FCS, and then resuspended at an appropriate concentration, for example in the region of 5×10$^4$ cells/ml. The target cells thus generated can then be employed in the CTL assay, for example by mixing them with the candidate effector cells in U-bottom 96 well-microtiter plates such that different effector to target cells (E:T) ratios are achieved.

Alternatively, as discussed above, target cells expressing the parent protein from which the test peptide was derived can be generated and used in the CTL assay. In this method, syngeneic cells are infected for 18-20 hours with an appropriate amount, such as 5×10$^7$ plaque forming units, of recombinant vaccinia virus containing the gene for the parent protein which is to be expressed. As a control, syngeneic cells may be infected with recombinant vaccinia virus which carries the gene for an immunologically unrelated protein. At this stage one may wish to confirm the presence of the required protein in the target cells, but not in the control cells, for example by western blotting both infected cell types with specific antibodies. Target cells created in this manner can then be labelled with the radioactive compound, in this case 100·Ci of $^{51}$Cr, and used in the chromium release CTL assay (Platsoucas & Good, 1981), as described above.

In certain embodiments where the candidate peptides to be screened are derived from the HIV protein gp160, the recombinant vaccinia virus system can be used to prepare cells which specifically express this protein. For use in this regard, the inventors have found the control (VSC8) and HIV env-expressing (VPE16) recombinant vaccinia viruses obtained through Dr. Bernard Moss via the AIDS Research and Reference Reagent Program, (Division of AIDS, NIAID, NIH) to be of particular use. To confirm the presence of the gp160 protein in such VPE16-infected P815 target cells, the inventors found it convenient to employ HIV antibody-positive human sera in the western blotting experiments. In using the VPE16-infected P815 target cells in CTL assays, the inventors determined that it was particularly advantageous to employ 5×10$^4$ target cells/ml and 1×10$^6$ candidate CTL effector cells/ml, mixed so as to obtain an initial E:T ratio of 20:1.

In CTL assays conducted using either of the above target cells, the percentage specific $^{51}$Cr-release can be calculated as:

$$100 \times \frac{(\text{experiment release} - \text{spontaneous release})}{(\text{maximum release} - \text{spontaneous release})}$$

The maximum release can be determined by measuring the radioactivity released into the supernatant from target cells in which complete lysis has been experimentally induced, such as by using a 5% solution of the non-ionic detergent Triton X-100 to disrupt the membranes of the cells. Spontaneous release can be determined by measuring the radioactivity released into the supernatant from target cells incubated without added effector cells. It is contemplated that valid experiments will have a value for spontaneous target lysis which is between 15-20% of the maximum lysis observed.

Prior to assaying the PLN cells for possible CTL activity, one may desire to first deplete certain cell populations, such as CD4$^+$ or CD8$^+$, from the mixture of cells. In this regard, re-stimulated PLN cells can be treated with either anti-CD4 monoclonal antibody (clone GK-1.5) plus complement (C) (+anti CD4+C), or anti-CD8 monoclonal antibody (clone 53-6.72) plus C (+anti CD4+C), as described by Platsoucas & Good (1981). It may also be desirable to treat certain PLN cells with complement alone (+C), to act as a comparison. Cells treated in any of these ways can then tested for their capacity to lyse MHC-matched target cells that have been pre-treated with the monomeric form of the peptide or infected with recombinant vaccinia virus expressing the parent protein from which the test peptide was derived.

Where one desires to identify CTL reactive compounds that do not exhibit an antibody generating capability, peptides identified as being T cell active may be screened to identify those that lack B cell stimulatory activity. Such peptides are proposed to be particularly useful in the preparation of vaccines for the treatment or prevention of viral diseases such as AIDS where an antibody response may in fact enhance infectivity of the causative agent. Identification of such peptides is accomplished by injecting a candidate into an immunocompetent animal (e.g., mice) to identify those peptides that fail to generate a significant antibody response to the native protein to whose sequence the peptides correspond in part. For example, in the case of HIV, one would desire to test for the production of antibodies having reactivity against gp12O, gp41 or core proteins, etc.

Of course, as mentioned above, the invention also concerns the identification of compounds capable of eliciting both a T cell response and a B cell response, in that this latter group will serve to induce protective antibody-based immunity in the immunized host.

CTL active compositions of the present invention prime T cells in a way that, when the infecting virus appears at a later date, memory T cells are activated to result in a cell-mediated immune response that destroys target cells that have the corresponding target protein or a portion thereof on their cell surfaces, and thereby the virus.

The inventors further optimized the above-described method for the generation of peptide-induced CTL responses against peptide immunogens. Particular objectives were to increase specific CTL production by lymphoid tissue more distant from the site of injection, such as in the spleen, and to improve the longevity of the response. It was determined that physically mixing peptides containing T helper epitope sequences with CTL-inducing peptides enhanced CTL responses in mice, both following multiple subcutaneous (sc) injections and single intradermal (id) injections in the footpad. In addition, the high level CTL response in the spleen was maintained for up to eight weeks after one id injection. An example of a suitable T helper peptide is C19A, having the sequence CRIKQIINM-WQGVGKAMYA (seq id no:2), which was found to effective in monomer, lipid tailed, and di-sulphide polymer forms.

The mechanism of enhancing a peptide-induced CTL response in vivo by peptides that induce T helper cells is not known. However, it is likely that the enhancing peptide, because of its ability to induce T helper cells, will result in increasing the levels of necessary cytokines that assist in the clonal expansion and dissemination of specific CTLs. Regardless of the underlying mechanism, it is envisioned that the use of mixtures of helper T cell and CTL-inducing peptides in immunization or vaccine formulations will greatly improve the capability of generating a systemic CTL response with a relatively long half life, compared to immunization with the CTL-inducing peptide(s) alone.

With regard to HIV, it is proposed that particularly useful peptides against which to generate a CTL responses will be those peptides which have sequences derived from the viral genes gag, pol, nef and env genes (Table 1), with env genes being particularly preferred. Even more preferably, peptides with sequences derived from the V3 loop of HIV gp120, such as those listed in Table 2 (SEQ ID NOS:11 through 27, respectively, and SEQ ID NO:1), may be employed as CTL-inducing peptides. It is envisioned that T helper cell-inducing epitopes for use in the present invention will generally have having an amphipathicity value of from about plus 10 to about plus 20.

Peptides and peptide combinations considered to be suitable as vaccines or components thereof may be tested in experimental animal models, such as mice, rats, rabbits, guinea pigs, goats, Rhesus monkeys, chimpanzees, and the like. Such tests will likely lead to the production of successful vaccines that induce cell-mediated immunity for protection against a variety of infectious agents.

Further aspects of this invention concern the identification and formulation of synthetic peptides as therapeutic agents for use against HIV, such that these chemically defined synthetic peptides will protect human cells from HIV-1 infection.

The V3 loop region of gp120 is known to be essential for HIV-1 infection of cells (Travis et al., 1991; Freed and Riser, 1987; Freed et al., 1991). Anti-V3 loop antibodies have been shown to inhibit HIV-1 cellular infection without interfering with gp120 binding to its cellular receptor, CD4 (Linsley et al., 1988; Javaherian et al. 1989). The V3 loop region is also known to be a target for a trypsin related protease on the host cell surface (Murakami et al., 1991). It has been speculated that after gp120 binds to CD4, the V3 loop is cleaved by a cell surface protease leading to a conformational change in the gp120/gp41 protein complex (McCune et al., 1988). Such a change may then expose the fusogenic domain in the transmembrane protein gp41, resulting in the fusion of the viral particle membrane with the cell membrane. The inventors therefore reasoned that V3 loop peptides may prevent infection of cells by inhibiting the cleavage of the gp 120 V3 loop.

Recent studies in this area have lead to the generation of conflicting results. Koito et al. (1989) reported that a synthetic peptide, corresponding to the major HIV-1 neutralizing epitope from the V3 loop of gp120, inhibits syncytium formation between the HIV-1 infected CCRF-CEM and uninfected Molt-4 cells in a dose-dependent manner. In these studies the 36 amino acid peptide (residues 303-338), CTRPNNNTRKSIRIQRGPGRAFVTIGKIGNMRQAHC (SEQ ID NO:45), representing the entire V3 loop, was found to inhibit syncytium formation by 30-60% at a concentration of 100·M (approximately 300·g/ml). However, a 24 amino acid peptide (residues 308-331, NNTRKSIRIQRG-PGRAFVTIGKIG SEQ ID NO:3) representing the middle portion of the V3 loop was less efficient and was required at 300·M concentration (approximately 720·g/ml) to achieve the same level of inhibition of syncytium formation. Neither of these peptides were tested for their capacity to inhibit HIV infection of cells.

In contrast, De Rossi et al. (1991) recently reported that synthetic peptides of 24 amino acids in length from V3 loop regions of different HIV-1 isolates actually enhance HIV-1 infection of cells through a CD4-dependent mechanism. In these experiments synthetic peptides at concentrations ranging between 0.62-20·M (approximately 1.5 to 48·g/ml) were employed and one human T cell line (Molt-3) was tested.

Despite the above evidence to the contrary, the present inventors proceeded to test the ability of V3 loop synthetic peptides to inhibit HIV infection. Synthetic peptides of varying length (8-24 amino acids) selected from the V3 loop of gp120 were determined to be surprising effective at inhibiting HIV infection of T cells, using both cultured human T cells such as H9, CEM and MT-4, and freshly prepared primary human T cells. These peptides include R15K, having the sequence RIQRGPGRAFVTIGK (seq id no:1), and N24G, having the sequence NNTRKSIRIQRG-PGRAFVTIGKIG (seq id no:3). The peptides termed D23 (SEQ ID NO:11), D24 (SEQ ID NO:12), D25 (SEQ ID NO:13), D26 (SEQ ID NO:14), D30 (SEQ ID NO:18), D35 (SEQ ID NO:23), D38 (SEQ ID NO:25), D39 (SEQ ID NO:26) and D40 (SEQ ID NO:27), the sequences of which are shown in Table 11A, were also found to inhibit HIV cellular infection.

An important discovery of this invention is the finding that peptides with sequences from a variety of different HIV isolates have the ability to inhibit HIV-1 IIIB infection of cells. These include H13N (HIGPGRAFYTTKN, seq id no:7) from HIV-1mn, and T13Q (TKGPGRVIYATGQ, seq id no:6) from HIV-1rf, along with the peptides detailed in Table 11A (SEQ ID NOS:11 through 14; 18; 23; 25 through 27 and 1; respectively). Importantly, it is contemplated that peptides with sequences which correspond to V3 loop sequences from other viral strains will also be useful in inhibiting infection by the homologous, or other related, HIV strains. As such, it is contemplated that peptides such as D27 (SEQ ID NO:15), D28 (SEQ ID NO:16), D29 (SEQ ID NO:17), D31 (SEQ ID NO:19), D32 (SEQ ID NO:20), D33 (SEQ ID NO:21), D34 (SEQ ID NO:22) and D37 (SEQ ID NO:24) (Table 11B) may still be found to be useful as infection-inhibiting peptides.

The inventors have previously shown the peptide EQL-WVTVYYGVPV (E13V, seq id no:4), from the amino-terminus of gp120 (residues 39-51) to be capable of inducing anti-HIV T helper cell responses in mice (Sastry & Arlinghaus, 1991). Antibodies against this peptide were found to be capable of binding denatured, but not native, gp120. On analyzing the ability of peptide E13V (seq id no:4) to interfere with HIV entry into cells, and thus to inhibit infection, the inventors found it, also, to be an effective infection-inhibitor peptide.

The infection-inhibitor peptides of the present invention, such as R15K (seq id no:1) and E13V (seq id no:4), are envisioned to be ideal candidates for inclusion in therapeutic formulations that will be effective in preventing infection of human cells by HIV-1. Of relevance to human therapy is the finding that R15K (SEQ ID NO:1), for example, retained full strength inhibitory activity after incubation in fetal calf serum for up to 4 hours. Since such formulations will be completely synthetic and defined, these reagents will be both economical and safe. Also, the V3 loop peptides as a mixture will provide the added advantage of being a immuno-therapeutic reagent because of the capacity of inducing HIV-1 specific CTL responses that can effectively kill all virus infected cells while preventing fresh infection of cells.

Thus, the present invention ultimately involves the preparation of both vaccines and therapeutic formulations including synthetic peptides. It is envisioned that the vaccines will include a peptide(s) bearing CTL-inducing epitopes, and ideally, will also include a peptide(s) bearing T helper cell-inducing epitopes. The therapeutic formulations may also, of course, include such sequences. However, peptides incorporating an HIV infection-inhibiting sequence are particularly preferred for use as components of such a therapeutic composition.

With regard to vaccination-type peptides of the present invention, it is contemplated that peptide multimers may be particular advantageous in the preparation of CTL-inducing vaccines in accordance herewith. Preferred multimers are formed of surfactant-like micelles and polymers. In addition to the amino-terminal lysyl residue, the spacer peptide can contain one to about five additional residues. Substantially any amino acid residue can be utilized so long as it does not interfere with the T cell immunizing capacity of an aqueous composition containing the multimer or with the capacity of the di-amide reaction product to form surfactant-like micelles in an aqueous composition. One to about three glycyl residues per spacer peptide are preferred.

The before-described peptide and the amino-terminal lysyl residue-containing peptide spacer are peptide-bonded together, and can thus be viewed as a composite polypeptide. The useful diamide is thus a reaction product of the alpha- and epsilon-amino groups of the amino-terminal lysyl residue and two moles per composite polypeptide of the $C_{12}$-$C_{18}$ fatty acid. The composite polypeptide can thus be prepared as a single sequence and amidified before or after removal from the resin, where solid phase synthesis is used, by conventional techniques.

The phrase "surfactant-like micelle" is used herein to emphasize that, in an aqueous composition, the di-amidolysyl composite polypeptide appears to form micelles similar to those formed by surfactants and to distinguish such multimers from submicroscopic structural units of protoplasm built up from polymeric molecules that are also sometimes referred to as micelles. The word "micelle" is also sometimes used herein, and when so used has the same meaning as surfactant-like micelle.

Another multimer form of a previously described peptide is a polymer having a plurality of peptide repeating units. In this case, a peptide containing two terminal cysteines as part of its natural sequence can be selected and synthesized. A peptide lacking such cysteines can be modified by the addition of one or two extra cysteines to the N- and C-terminal ends, respectively. The presence of two cysteines per peptide permits polymerization of the subunit peptide by air oxidation to form oxidized cysteine(cystine)-linked polymers and/or cyclic peptides. Such multimers enhance immune recognition of the peptide without the need of a carrier.

The lysine-terminated spacer peptide can contain one to about five amino acid residues in addition to the lysyl residue, and the one or two added terminal cysteine residues are not included in counting the length of a peptide of the present invention. A peptide containing terminal cysteine residues is referred to as a di-cysteine-terminated peptide or more simply, a di-Cys peptide. Details for preparing polymers containing di-Cys peptide repeating units are provided hereinafter.

Aqueous compositions (inocula) of the present invention comprise an immunologically effective amount of a CTL-inducing, T helper cell-inducing, or HIV infection-inhibiting peptide or peptides, whether in multimeric form or not, dissolved or dispersed in a pharmaceutically acceptable aqueous medium. Such compositions are also referred to as inocula.

The phrase "pharmaceutically acceptable" refers to molecular entities and compositions that do not produce an allergic or similar untoward reaction when administered to a human.

The preparation of an aqueous composition that contains an immunizing molecule such as a peptide or multimer, or an infection-inhibiting component, such as a peptide, as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A peptide or peptide multimer can be formulated into a composition in a neutral or salt form. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Upon formulation, vaccines will be administered in a manner compatible with the dosage formulation, and in such amount as is immunologically effective. As used herein, "immunologically effective amount" means an amount of composition is used that contains an amount of a peptide, peptides, or peptide multimers sufficient to induce an effective CTL response in the host animal (mammal) such as by the induction of specifically targeted cytotoxic T cells. In preferred embodiments, it is contemplated that the immunologically effective vaccine composition will also include an amount of a peptide, peptides, or peptide multimers effective to induce T helper cell activity and to thus enhance the CTL effect. The presence of such cytotoxic T cells is assayed as discussed hereinafter.

In the context of a vaccine, the quantity of peptide(s) and volume of composition to be administered depends on the host animal to be immunized, the capacity of the host animal's immune system to activate T cells, and the degree of protection desired. Precise amounts of active peptide multimer required to be administered depend on the judgment of the practitioner and are peculiar to each individual. However, suitable dosage ranges are of the order of about 10 micrograms (·g) to about 500 milligrams (mg), preferably about 50·g to about 1 mg, and more preferably about 100·g of active ingredient peptide multimer per individual. A minimal volume of a composition required to disperse the immunizing amount of peptide multimer is typically utilized. Suitable regimes for initial administration and booster shots are also variable, but are typified by an initial administration followed in one or two week intervals by a subsequent injection or other administration.

A composition can also include an adjuvant as part of the excipient. Adjuvants such as complete Freund's adjuvant (CFA), incomplete Freund's adjuvant (IFA) for use in laboratory host mammals are well known in the art, and are used illustratively herein. Pharmaceutically acceptable adjuvants such as alum can also be used.

The following examples are included to demonstrate preferred embodiments of the invention. It will be appreciated by those of skill in the art that the techniques disclosed in the examples which follow represent techniques discovered by the inventors to function well in the practice of the invention, and thus can be considered to constitute preferred modes for its practice. However, those of skill in the art will, in light of the present disclosure, appreciate that many changes can be made in the specific embodiments which are disclosed and still obtain a like or similar result without departing from the spirit and scope of the invention.

EXAMPLE 1

Preparation of Peptides, Peptide Polymers and Peptide Micelles

Synthetic peptides of 7 to about 30 amino acid residues in length were prepared corresponding to the selected conserved domains of the core and gp16O (gp12O and gp41) molecules using the solid-phase technique of Merrifield (1963) using a modified Vega 250 automated peptide synthesizer or by the "bag" method described in Houghten (1985). In either case, removal of the t-butyloxycarbonyl (t-BOC) amino acid blocking groups and the hydrolysis of the peptide from the resin were carried accomplished by hydrofluoric acid (HF) treatment at 0·C for one hour. The peptide-containing mixture was then extracted with diethyl ether to remove non-peptide organic compounds and the synthesized peptides were extracted from the resin with 25% acetic acid (w/v).

Various synthetic peptides have been prepared by this procedure, including nineteen (19) that correspond to conserved domains of the gp12O molecule and the gp41 molecule, as listed in Table 3 (SEQ ID NOS:4, 28 through 43, 2 and 44, respectively). The synthesized peptides correspond to designated conserved domains (regions) of gp16O in HIV as shown.

TABLE 3

AMINO ACID SEQUENCE OF SYNTHETIC PEPTIDES

| PEPTIDE # | AMINO ACID SEQUENCE[1] | LOCATION IN HIV[2] ENVELOPE |
|---|---|---|
| 103 | $^{39}$EQLWVTVYYGVPV$^{51}$ | GP160-CR-1 |
| 104 | $_{45}$VYYGVPVWKEA$^{55}$ | GP160-CR-1 |
| 105 | $_{48}$GVPVWKEATTLFC$_{61}$ | GP160-CR-1 |
| 106 | $^{72}$AHKVWATHACV$^{82}$ | GP160-CR-1 |
| 107 | $^{81}$CVPTNPVPQEVV$^{92}$ | GP160-CR-1 |
| 108 | $^{92}$VLENVTENFNM$^{102}$ | GP160-CR-1 |
| 109 | $^{105}$NNMVEQMHEDI$^{116}$ | GP160-CR-1 |
| 110 | $^{109}$EQMHEDIISLWDQ$^{121}$ | GP160-CR-1 |
| 111 | $^{118}$LWDQSLKPCVKLT$^{130}$ | GP160-CR-1 |
| 112 | $^{121}$SLKPCVKLTPLC$^{133}$ | GP160-CR-1 |
| 113 | $^{204}$SVITQACSKVSFE$^{216}$ | GP160-CR-2 |
| 114 | $^{215}$FEPIPIHYCAFPGF$^{228}$ | GP160-CR-2 |
| 115 | $^{236}$KKFNGTGPCTN$^{246}$ | GP160-CR-2 |
| 116 | $^{240}$GTGPCTNVSTVQC$^{252}$ | GP160-CR-2 |
| 117 | $^{250}$VQCTHGIRPVVSTQ$^{263}$ | GP160-CR-2 |
| 61 | $^{586}$YLRDQQLLGIWGC$^{598}$ | GP160-CR-5 |
| 63 | $^{519}$FLGFLGAAGSTMGAASL-TLTVQANQ$^{543}$ | GP160-CR-5 |
| 65 | $^{417}$CRIKQIINMWQGVGKAMYA$^{435}$ | GP160-CR-3 |
| 67 | $^{417}$CRIKQIINMWQGVGKAM-YAPPIGGQIRC$^{444}$ | GP160-CR-3 |

[1]The N- and C-terminal amino acid residues of each peptide are numbered as to their position in the gp160 amino acid residue sequence according to Modrow et al. Virol., 61:570 (1987). A dash (-) indicates that the sequence continues on the next line. The peptides in this table are represented by SEQ ID NOS:4, 28 through 43, 2 and 44, respectively.
[2]CR = Conserved Region Two types of high molecular weight (multimeric) forms of the peptides listed in Table 3 were prepared. The principal form of multimer was a di-cysteine (di-Cys terminated) polymer in which a plurality of peptides were linked end-to-end by disulfide bonds. These di-cysteine polymers were produced by adding cysteine residues to the termini of each peptide during synthesis. The di-cysteine-terminated (di-Cys) peptides were then dissolved (10 mg/ml) in ammonium bicarbonate (0.1M) at room temperature (·25·C) and stirred for about 16 hours to effect oxidation of the sulfhydryl groups to produce polymer forms of the peptides. The peptide solution was freeze-dried and analyzed by HPLC to confirm the presence of polymer forms of the peptide.

The second type of high molecular weight form produced was a surfactant-like micelle formed by linkage of an amino-terminal lysine-containing spacer peptide (Lys-Gly-Gly-) to the peptide sequence to form a composite polypeptide, and then coupling a $C_{12}$-$C_{18}$ fatty acid, such as palmitic acid, to both the alpha and epsilon amino groups, as in Hopp (1984). The $C_{12}$-$C_{18}$ fatty acid-containing peptides produced are then extracted in 95% acetic acid and utilized to form large micelles in the aqueous composition that exhibit increased immunogenicity relative to the peptides.

Di-Cys polymer multimers of all of the peptides listed in Table 3 were prepared. Aqueous peptide micelle multimers have been prepared of peptides designated 61 (SEQ ID NO:42), 63 (SEQ ID NO:43), 65 (SEQ ID NO:2) and 67 (SEQ ID NO:44), and are designated as peptides 62, 64, 66 and 68, respectively. Peptides designated 103 through 117 (SEQ ID NOS:4 and 28 through 41, respectively) were utilized only in their di-Cys polymer multimeric forms.

The high molecular weight, multimeric forms produced correspond to multiple copies of specific regions of gp12O and gp41 in HIV. For ease of designation, the multimer forms will be designated by the peptide number from which it is composed—that is, peptide 61 (SEQ ID NO:42) refers to the di-Cys multimeric (polymeric) form of peptide 61 (SEQ ID NO:42) and peptide 66 refers to the aqueous micelle form of peptide 65 (SEQ ID NO:2), whereas peptide 103-117 refers to a polymeric multimer.

Peptides 65 (SEQ ID NO:2) and 66 correspond to the region of gp12O that binds to the cell surface T4 receptor. Peptides 61 (SEQ ID NO:42) and 62 correspond to a region near the amino-terminal portion of gp41 that represents a major immunodominant epitope seen by AIDS patients' sera.

EXAMPLE 2

Anti-Peptide Antibody Response

Aqueous compositions of the multimers; i.e., the di-Cys peptide polymers and micelles produced in EXAMPLE 1 were assayed for their ability, or lack of ability to elicit an anti-peptide antibody response in BALB/c mice, an immunocompetent mouse strain.

Groups of BALB/C mice (6-8-week-old females, 3 to 5 mice/group, Charles River Laboratories) were immunized by subcutaneous (s.c.) or intraperitoneal (i.p.) injection of a peptide multimer (100·g/injection) in complete Freund's adjuvant (CFA) (1:1 ratio). Booster injections (50·g of peptide multimer) in incomplete Freund's adjuvant (IFA) (1:1) were given at 6 and 10 weeks after the initial immunization. Each mouse was bled from its retro-orbital plexus at two-week intervals and the serum was pooled for individual mice in each group.

An ELISA assay was performed on each serum to detect the presence of anti-peptide antibodies utilizing peroxidase-conjugated goat anti-mouse IgG (Boehringer Mannheim Biochemicals, Indianapolis, Ind.) as the second antibody. Preliminary results for peptides 61-68 (peptide 61, SEQ ID NO:42, peptide 63, SEQ ID NO:43, peptide 65, SEQ ID NO:2, peptide 67, SEQ ID NO:44) are shown in Table 4, whereas further refined results for peptides peptide 61, SEQ ID NO:42, peptide 63, SEQ ID NO:43, peptide 65, SEQ ID NO:2, peptide 67, SEQ ID NO:44) and 103-117 (SEQ ID NOS:4, 28 through 41, respectively) are shown in Table 5. It was found that the high molecular weight forms of peptides 65 (SEQ ID NO:2), 66, 67 (SEQ ID NO:44), 68, 105 (SEQ ID NO:29), 106 (SEQ ID NO:30), 107 (SEQ ID NO:31), 108 (SEQ ID NO:32), 109 (SEQ ID NO:33), 110 (SEQ ID NO:34), 112 (SEQ ID NO:36), 114 (SEQ ID NO:38), 115 (SEQ ID NO:39) and 117 (SEQ ID NO:41) elicited high antibody titers, whereas peptides 61 (SEQ ID NO:42), 62, 63 (SEQ ID NO:43), 64, 103 (SEQ ID NO:4), 104 (SEQ ID NO:28), 111 (SEQ ID NO:35), 113 (SEQ ID NO:37) and 116 (SEQ ID NO:40) produced very low to negligible amounts of anti-peptide antibodies. Similar results were obtained for antibody responses in B6C3 F1 mice (Charles River Laboratories), another immunocompetent strain.

Some of the sera were further assayed for antibody response (reactivity) with native gp160, and the results, shown in Table 6, demonstrate that these peptides do not represent B cell epitopes since there was no immunoreaction with native gp160.

TABLE 6

T AND B CELL RESPONSES IN MICE TO HIV ENVELOPE GP160 DERIVED SYNTHETIC PEPTIDE IMMUNOGENS

| Peptide Immunogen | In Vitro Proliferation of PLN Cells from* | | | | Antipeptide Antibody Reactivity to** | |
|---|---|---|---|---|---|---|
| | $B_6C_3F_1$ | | A SW × Balb/c $F_1$ | | | |
| | Analogous Peptide | GP 160 | Analogous Peptide | GP 160 | Analogous Peptide | GP 160 |
| 61 | ++ | + | ++ | ++ | − | − |
| 63 | ++ | ++ | ++ | ++ | • | − |
| 65 | ++ | + | ++++ | ++ | ++ | − |
| 67 | ++ | − | ++++ | ++ | +++ | − |
| 103 | + | + | +++ | + | − | − |
| 104 | ++++ | ++ | +++ | + | • | − |
| 105 | ++++ | +++ | + | − | • | − |
| 106 | +++ | + | ++++ | + | ++ | − |
| 107 | ++ | ++ | + | + | + | − |
| 108 | + | + | + | − | + | − |

TABLE 4

ANTIBODY RESPONSE OF VARIOUS PEPTIDES IN BALB/C MICE
ELISA Titer in Bleed 1

| Peptide 1 | Pre-Immune | 1 | 2 | 3 | 4 | 5 | 6 | 7 | 8 |
|---|---|---|---|---|---|---|---|---|---|
| 61 | 1:40 | 1:400 | 1:100 | 1:100 | a:100 | 1:100 | 1:400 | 1:200 | 1:400 |
| 62 | 1:20 | 1:100 | 1:100 | 1:100 | 1:100 | 1:100 | 1:200 | 1:100 | 1:100 |
| 63 | 1:40 | 1:80 | 1:20 | 1:40 | 1:320 | 1:80 | 1:80 | 1:320 | 1:5120 |
| 64 | 1:20 | 1:40 | 1:40 | 1:00 | 1:40 | 1:40 | 1:40 | 1:40 | 1:40 |
| 65 | 1:40 | 1:80 | 1:800 | $1:1 \times 10^4$ | $1:5 \times 10^4$ | $1:2 \times 10^4$ | $1:2 \times 10^5$ | $1:2 \times 10^5$ | $1:2 \times 10^5$ |
| 66 | 1:40 | 1:160 | $1:6 \times 10^3$ | $1:1 \times 10^5$ | $1:1 \times 10^5$ | $1:1 \times 10^5$ | $1:2 \times 10^4$ | $1:5 \times 10^4$ | $1:5 \times 10^5$ |
| 67 | 1:40 | 1:160 | $1:3 \times 10^3$ | $1:2 \times 10^4$ | $1:2 \times 10^4$ | $1:1 \times 10^5$ | $1:8 \times 10^5$ | $1:1 \times 10^5$ | $1:2 \times 10^5$ |
| 68 | 1:80 | 1:1600 | $1:1 \times 10^4$ | $1:1 \times 10^4$ | $1:1 \times 10^5$ | $1:1 \times 10^5$ | $1:4 \times 10^5$ | $1:4 \times 10^5$ | $1:4 \times 10^5$ |

In this table peptides 61, 63, 65 and 67 are represented as SEQ ID NOS: 42, 43, 2 and 44, respectively.

TABLE 5

ANTIBODY RESPONSE OF VARIOUS PEPTIDES IN BALB/C MICE

| PEPTIDE | ELISA TITER |
|---|---|
| #62 AA 586-598 | 1:400 |
| #63 AA 519-543 | 1:5120 |
| #65 AA 417-435 | $1:2 \times 10^5$ |
| #67 AA 417-444 | $1:82 \times 10^5$ |
| #103 AA 39-51 | 1:640 |
| #104 AA 45-55 | 1:2000 |
| #105 AA 48-61 | 1:5000 |
| #106 AA 72-82 | $1:4 \times 10^5$ |
| #107 AA 81-92 | $1:1 \times 10^5$ |
| #108 AA 92-102 | $1:1 \times 10^5$ |
| #109 AA 105-116 | $1:8 \times 10^5$ |
| #110 AA 109-121 | $1:6 \times 10^5$ |
| #111 AA 118-130 | 1:80 |
| #112 AA 121-133 | $1:1 \times 10^5$ |
| #113 AA 204-216 | 1:640 |
| #114 AA 215-228 | $1:1 \times 10^6$ |
| #115 AA 236-246 | $1:4 \times 10^5$ |
| #116 AA 240-252 | 1:640 |
| #117 AA 250-263 | $1:8 \times 10^6$ |

In this table peptides 63, 65, 67 and 103-117 are represented by SEQ ID NOS:43, 2, 44, 4 and 28 through 41, respectively.

TABLE 6-continued

T AND B CELL RESPONSES IN MICE TO HIV ENVELOPE GP160 DERIVED SYNTHETIC PEPTIDE IMMUNOGENS

| Peptide Immunogen | In Vitro Proliferation of PLN Cells from* | | | | Antipeptide Antibody Reactivity to** | |
|---|---|---|---|---|---|---|
| | $B_6C_3F_1$ | | A SW × Balb/c $F_1$ | | | |
| | Analogous Peptide | GP 160 | Analogous Peptide | GP 160 | Analogous Peptide | GP 160 |
| 109 | ++ | • | • | + | +++ | − |
| 110 | ++ | − | ++ | + | ++++ | − |
| 111 | + | ++ | • | − | − | − |
| 112 | + | + | + | + | + | − |
| 113 | ++ | + | ++ | + | − | − |
| 114 | ++ | − | ++ | + | ++++ | − |
| 115 | ++ | + | •ND | ND | ++ | − |
| 116 | ++ | − | ND | ND | − | − |
| 117 | +++ | − | ND | ND | ++++ | − |

*cpm values are corrected and categorized according to unrelated antigen response in vitro.
**Antibody raised in Balb/C mice, reactivity measured by ELISA and categorized according to the end point.
•Not determined.
In this table peptides 63, 65, 67 and 103-117 are represented by SEQ ID NOS: 43, 2, 44, 4 and 28 through 41, respectively.

EXAMPLE 3

T Cell Responses

The high molecular weight, multimeric di-Cys peptide polymeric forms of the peptides described in EXAMPLE 1 were assayed for their elicitation of a T cell proliferative response as in Millich et al. (1985).

Mice (3 or 5 mice/group) were injected in the right hind footpad with a 1:1 mixture of peptide polymer (100·g/injection) and CFA. Peptides 61, 63, 65 and 67 (SEQ ID NOS:42, 43, 2 and 44, respectively) were injected into B6C3 F1 mice (H-$2^{kxb}$, Charles River Laboratories) and A.SWX-BALB/C F1 mice (H-$2^{sxd}$, Jackson Labs, Bar Harbor, Me.). Draining popliteal lymph node (PLN) cells were harvested after ten (10) days, and cultured ($2\times10^5$ cells/well) in 96-well microtiter plates in 0.2 ml of Click's medium (Click et al., 1972) containing various concentrations of synthetic peptide, gp16O, an unrelated proteinaceous material or medium alone, for 96 hours at 37·C in a humidified atmosphere of 5% $CO_2$. During the final 16-18 hours of culturing, $^3$H-thymidine ($^3$H-TdR) (1·Ci/well, 6-7 Ci/mmole, ICN Radiochemicals) was added. The cells were harvested onto filter strips and $^3$H-TdR incorporation was monitored.

Results from such studies were expressed as a stimulation index (SI) representing the fold increase in radioactivity counts in the presence of antigen compared to background values where no antigen was added. The SI values with the different peptides were compared to that obtained with tuberculin purified protein derivative (PPD) as a positive control antigen.

The peptide-specific $^3$H-TdR incorporation for T cell responses (delta cpm) in mice with the differing major histocompatibility (MHC) haplotypes, B6C3 F1 (C57B1/6xC$^3$H/HcJ) and (A.SWxBALB/c) F1, were determined for all of the synthetic peptides. The $^3$H-TdR incorporation values represent the difference between the radioactivity values obtained in wells containing antigen and in control wells without added antigen. The non-specific proliferation of PLN cells was determined by including an unrelated peptide in the assays, shown as a horizontal bar for each peptide.

All of the assayed peptides were found to exhibit good T cell proliferative responses in B6C3 F1 mice, whereas all of the assayed peptides, except peptides 105 (SEQ ID NO:29), 107 (SEQ ID NO:31), 109 (SEQ ID NO:33) and 111 (SEQ ID NO:35), exhibited good T cell proliferative responses in A-SWxBALB/c F1 mice.

It was demonstrated by the results above and those described in EXAMPLE 2 that peptides 61 (SEQ ID NO:42), 63 (SEQ ID NO:43), 103 (SEQ ID NO:4) and 113 (SEQ ID NO:37) do not stimulate anti-peptide antibody production but are very good immunogens, in their disulfide (di-Cys) polymeric form, for eliciting a strong T cell response directed against both the corresponding peptide and the native HIV envelope protein gp16O.

T cell proliferation measured by $^3$H-TdR incorporation, was also similarly assayed as a function of the T cell antigen concentration, using various amounts of native gp12O or gp16O as one control, and PPD as another control. PLN from B6C3 F1 mice were used in these studies.

EXAMPLE 4

Induction of HIV-Specific Cytotoxic T Lymphocytes

Groups of 3 to 5 syngeneic female mice (6 to 8 weeks of age) are immunized by intradermal injection in an appropriate site with an aqueous composition containing an immunizing (CTL-stimulating) amount of peptide either as monomer or as the before-discussed multimers in CFA (1:1). Ten (10) days after immunization, draining PLN cells and spleen lymphocytes are obtained and restimulated in vitro by culturing for six (6) days with irradiated syngeneic normal spleen cells that were pre-treated with the same synthetic peptide as immunogen.

The presence of cytotoxic T lymphocytes (CTL) is determined by a 4-hour $^{51}$Cr release assay as follows. The PLN cells are maintained for five days at 37·C in Clicks medium containing 10% fetal calf serum (FCS) together with irradiated syngeneic normal spleen cells that were pre-treated with the appropriate test peptide. These cells are designated as the effector cells, and express H-$2^d$ MHC class I antigen.

Target cells (phytohaemagglutinin-stimulated (PHA) blasts of syngeneic mouse spleen cells or P815 mouse cells expressing a corresponding HIV protein) are washed three times with serum-free RPMI 1640 medium and then admixed, contacted and maintained (incubated) at 37·C for about 1.5 to about 2 hours together with 250·Ci of sodium chromate (specific activity 200-400 Ci/g of $^{51}$Cr, New England Nuclear, Boston, Mass.). The target cells are subsequently washed with RPMI 1640 medium containing 10% FCS, and resuspended in RPMI 1640 with 10% FCS and different concentrations of peptide. These cells are then washed 3 times with RPMI containing 10% FCS and resuspended at $5\times10^4$ cells/ml. A 100·1 aliquot of each cell suspension is added to a well of a 96-well-U-bottom microtiter plate.

A 100·1 aliquot of the appropriate effector cell suspension ($5\times10^6$ cells/ml) is added to each well and a twofold serial dilution made to obtain different effector-to-target cell (E:T) ratios. Control wells receive 0.1 ml of RPMI medium with 10% FCS alone in the absence of effector cells to obtain a value for spontaneous $^{51}$Cr release, and receive 0.1 ml of 5% Triton X-100 detergent to obtain a value for maximum $^{51}$Cr release.

The plates are incubated at 37·C for about 4 hours, following which 100·1 of supernatant from each well is monitored in a gamma counter to determine $^{51}$Cr release. The percent cytotoxicity is calculated as $$\frac{(\text{Effector Cell} - \text{Stimulated Release}) - (\text{Spontaneous Release})}{\text{Maximum Release} - \text{Spontaneous Release}} \times 100$$

EXAMPLE 5

Rapid assay of HIV-specific CTLs Induced by an Immunodominant Peptide

A peptide with the sequence RIQRGPGRAFVTIGK, herein referred to as R15K (seq id no:1), from the HIV gp160 immunodominant V3 loop has previously been identified as a CTL immunodominant epitope in H-$2^d$ mice (Takahashi et al., 1988). In the original studies, CTLs induced in vivo by infecting Balb/c mice with recombinant vaccinia virus expressing HIV env proteins, were shown to lyse syngeneic target cells pre-incubated with R15K (SEQ ID NO:1). Unfortunately, to date, studies in which mice were immunized with free R15K (SEQ ID NO:1) peptide have been reported to be unsuccessful in inducing CTLs (Berzofsky, 1991).

Accordingly, the present inventors sought to examine the induction of CD8+ HIV R15K-specific CTLs in 6-8 week old Balb/c mice by employing differing sites of inoculation, differing forms of the peptide, and recovering the effector cells from different tissue origins. It was observed that draining popliteal lymph nodes (PLN) of mice immunized in the hind-foot pad with 100·g of the R15K peptide (seq id no:1), in a 1:1 emulsion with CFA, were the best source of CTL effectors against irradiated (3300 rads) syngeneic target cells preincubated with monomeric R15K (SEQ ID NO:1) (40·g/ml for 2 h at 37·C). This has particular importance and physiological significance because human lymph nodes have been described as the primary site of HIV replication (Kaneshima et al., 1991; Fauci 1991). An important aspect of this immunization protocol is that CTLs could be recovered by mild homogenization from PLN surgically removed after only 10 days.

To determine the optimal form of the peptide for consistent induction of peptide-specific CTLs in vivo, the R15K peptide (seq id no:1) was prepared in three different configurations: a) linear monomer, b) disulfide-linked polymer formed by oxidation of cysteine residues added at both the N- and C-termini and c) micelles formed by conjugating the peptide to a dipalmityl-lysine-glycine-glycine at the N-terminus (Hopp, 1984; Sastry & Arlinghaus, 1991). It was found that a single immunization of Balb/c mice in the hind-foot pad with any of the above R15K (SEQ ID NO:1) forms in CFA consistently resulted in generation of CTLs which specifically lysed MHC-matched target cells (P815, H-2$^d$) pre-incubated with the peptide. Such responses were observed in 8 of 12 mice immunized with the monomeric form, in 13 of 13 mice immunized with the micelle form and 6 of 8 mice immunized with the disulfide polymer form of the peptide. Lysis of MHC-matched target cells without peptide pre-treatment (P815) was not observed. Representative results are shown in FIG. 1.

Figure 2A:
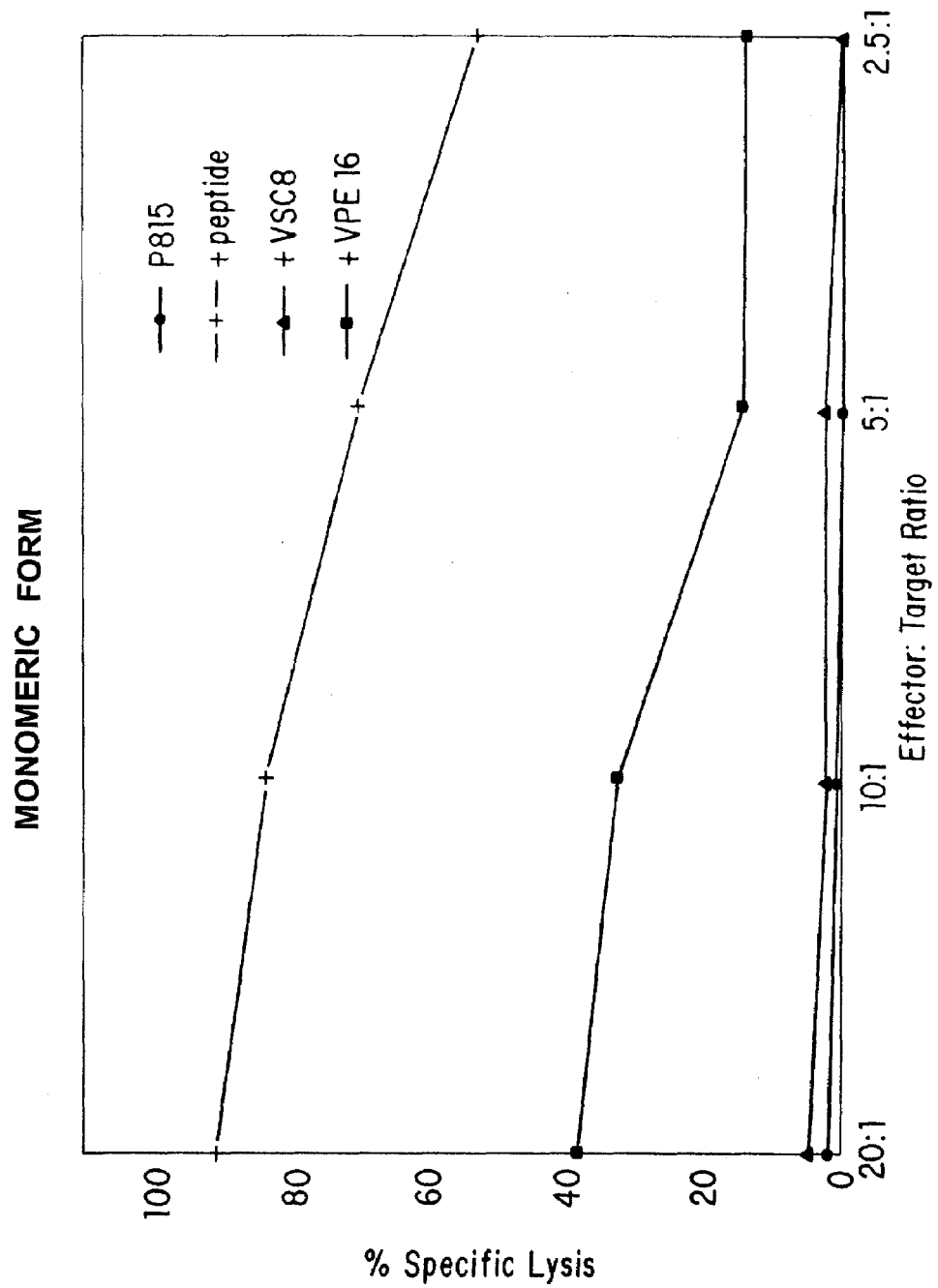
FIG. 2. CTLs from Balb/c mice immunized in vivo with any R15K-type peptides recognize MHC-matched target cells that were either pre-treated with peptide monomers (P815+ peptide) or infected with recombinant vaccinia virus expressing the HIV IIIB envelope protein, gp160 (P815+ VPE16). Immunization of mice and peptide pre-treatment of P815 target cells was carried out as in FIG. 1. 5×10$^6$ P815 target cells were infected with 5×10$^7$ plaque forming units of control (VSC8) or recombinant vaccinia virus expressing HIV envelope protein (VPE16) for 18-20 hours prior to labelling with 100·Ci of $^{51}$Cr (ICN Radiochemicals, Irvine, Calif.). The cytotoxic activity was determined by $^{51}$Cr-release assay (Platsoucas & Good, 1981).
Figure 2B:
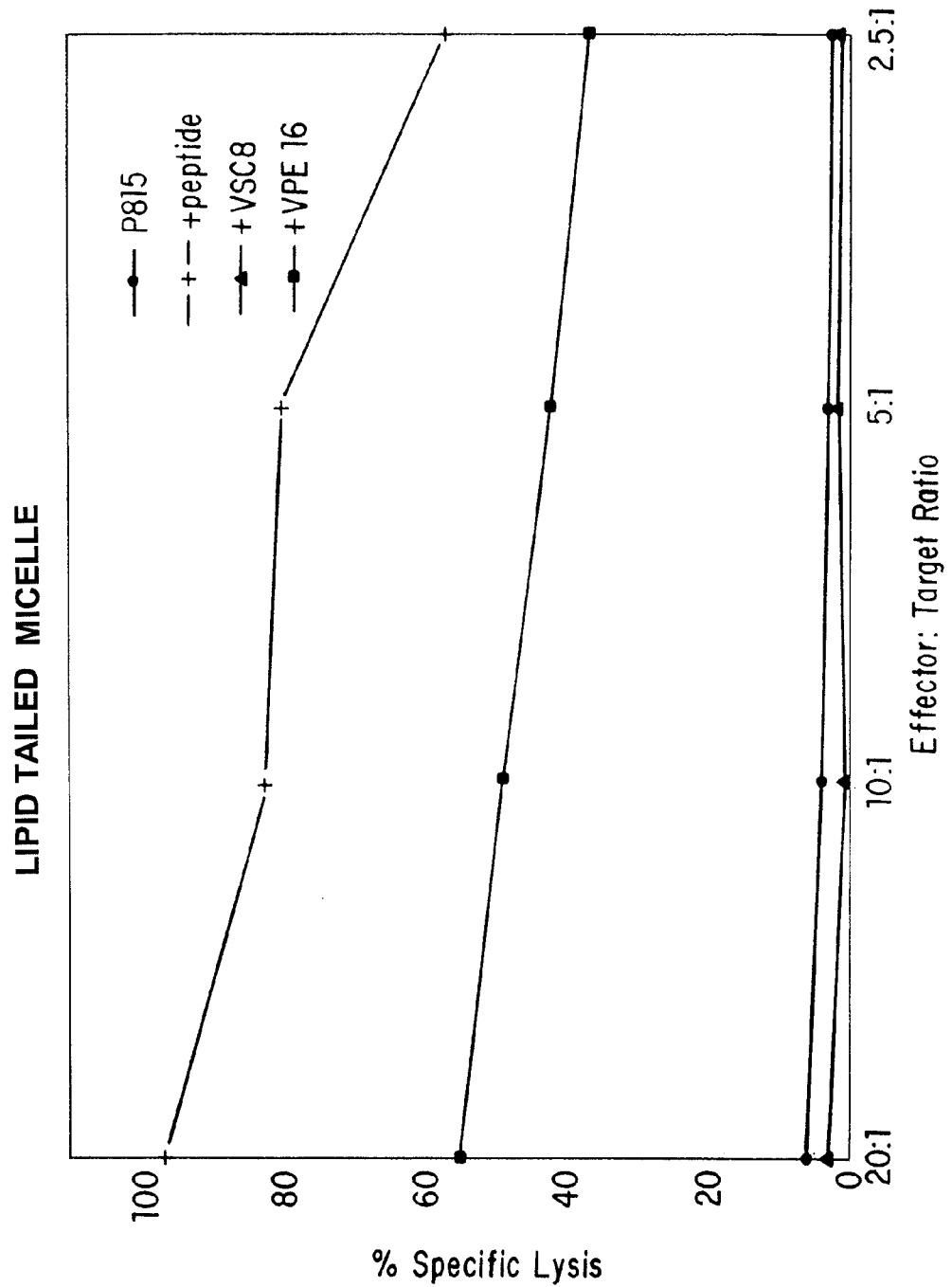

The CTLs induced by all three forms of the peptide also specifically lysed P815 cells infected with a recombinant vaccinia virus expressing HIV gp160 (VPE16), but not cells infected with a control vaccinia virus (P815+VSC8) (FIG. 2). Western blotting with HIV antibody-positive human sera confirmed the presence of gp 160 protein in VPE16-infected, but not in VSC8-infected P815 target cells. The peptide-induced CTLs in Balb/c mice were H-2 restricted. They lysed only peptide pre-treated H-2$^d$ target cells (P815) but not peptide-treated 3A9 target cell, which are expressing the H-2K haplotype (Table 7).

Representative results with CTLs generated in mice immunized with the micelle form of R15K (seq id no:1) peptide are shown in Table 7. Similar results were obtained with CTLs induced by injection of the monomeric and polymeric forms of the R15K (SEQ ID NO:1) peptide.

Figure 3A:
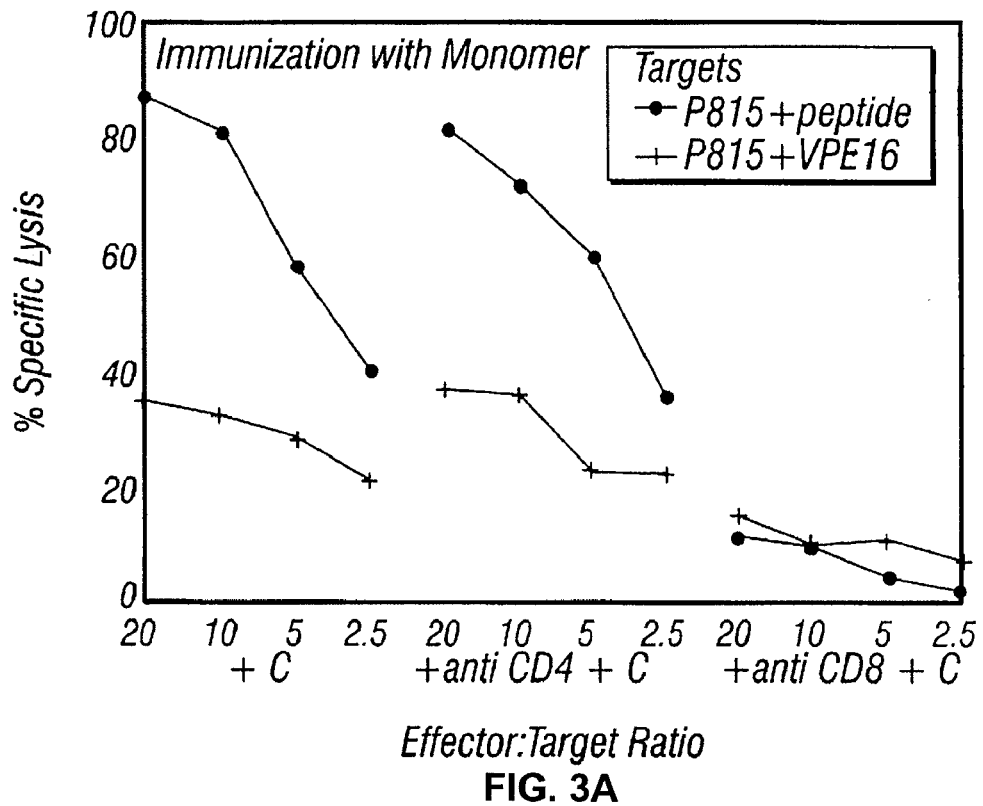
FIG. 3. CTLs primed by in vivo immunization with either the monomeric form or the lipid-tailed micelle form of the HIV V3-loop RISK peptide are CD8-positive. Re-stimulated PLN cells (as in FIG. 1) were treated with complement along (+C) or with either anti-CD4 monoclonal antibody (clone GK-1.5) plus C (+anti CD4−C) or anti-CD8 monoclonal antibody (clone 53-6.72) plus C (+anti CD8+C) as in (Platsoucas & Good, 1981). Resulting cells were then tested for their capacity to lyse MHC-matched target cells that were either pre-treated with the monomeric form of the peptide (P815+ peptide) or infected with recombinant vaccinia virus expressing HIV IIIB envelope protein gp160 (P815+ VPE16).
Figure 3B:
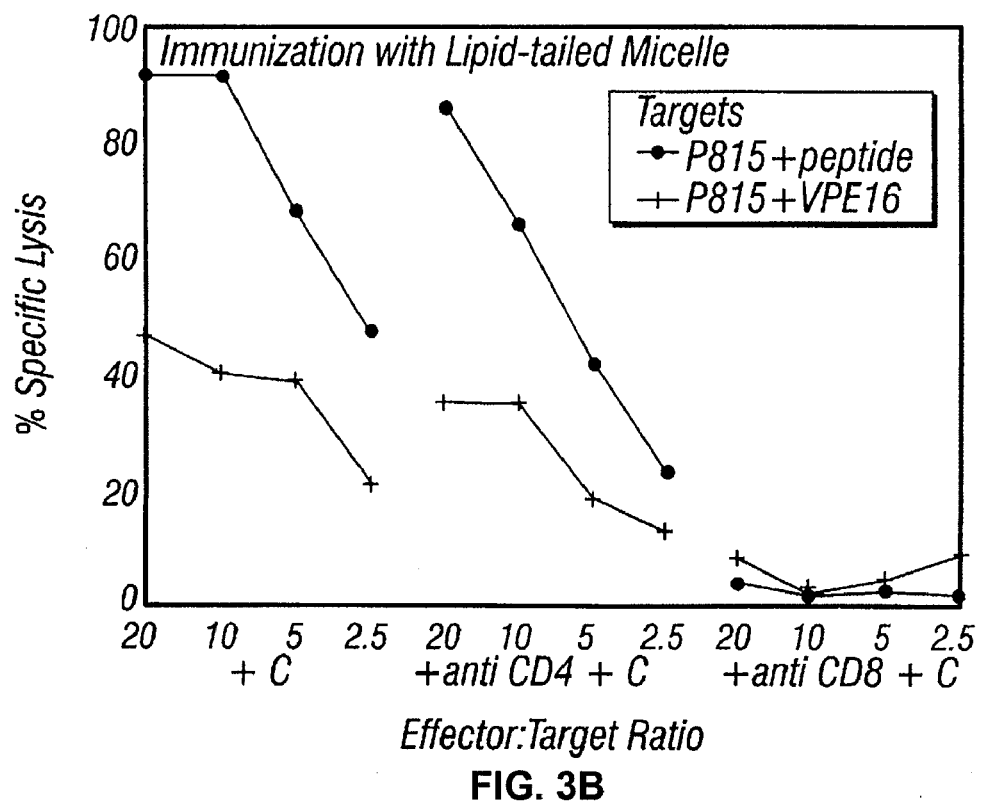

Experiments were performed to determine whether the virus-specific CTLs were CD8+ or CD4+. Treatment of the CTL effectors from mice immunized with monomeric peptide with anti-CD8 monoclonal antibodies (MAbs) and rabbit complement abolished the cytotoxicity against peptide treated, or env expressing, targets (FIG. 3A). In contrast, pre-treatment of effector cells with anti-CD4 MAbs plus complement, or complement alone, had no significant effect. Similar results were also obtained with CTLs generated in mice immunized with the peptide in micelle (FIG. 3B) and polymeric forms. The induction of CD8+ CTLs by R15K (seq id no:1) is consistent with the use of P815 target cells which express MHC class I, but not class II, gene products (Maryanski et al., 1985). MHC class I-restriction is commonly observed with CD8+ effector CTLS.

Since the CTL epitope studied in the present investigation is in the middle of an immunodominant B-cell active region of the HIV gp120, the B-cell activity of the R15K (SEQ ID NO:1) peptide was investigated. Either as monomer or lipid tailed micelle or after conjugation to KLH, this peptide failed to induce in mice a measurable titer of anti-peptide antibody. However, the mice immunized with peptide conjugated to KLH did make antibodies against KLH, showing that the mice are immunocompetent. Sera from mice immunized in the foot pad were also tested, when it was observed that no anti-peptide antibodies were formed.

TABLE 7

Peptide and Target Cell Specificity of CTL's induced in Balb/C Mice by the HIV env V3-Loop R15K Peptide (seq id no:1)

| Target Cells | % Specific Lysis at Various E:T$^a$ Ratios | | |
|---|---|---|---|
| | 100:1 | 50:1 | 25:1 |
| P815$^b$ | 7.2 | 0 | 0 |
| P815 + A84$^c$ | 76.7 | 67.2 | 65.9 |
| P815 + B106$^d$ | 4.2 | 0.6 | 0 |
| P815 + B105$^e$ | 6.7 | 0 | 0 |
| 3A9$^f$ | 7.0 | 0.6 | 0 |
| 3A9 + A84$^g$ | 10.0 | 8.0 | 0 |

$^a$ = Effector to target cell ratio
$^b$ = MHC-matched target cells (H-2$^d$)
$^c$ = H-2$^d$ cells pre-treated with HIV env V3-loop R15K peptide
$^d$ = H-2$^d$ cells pre-treated with a Influenza virus peptide
$^e$ = H-2$^d$ cells pre-treated with a Sendai virus peptide
$^f$ = MHC-mis-matched target cells (H-2$^k$)
$^g$ = H-2$^k$ target cells pre-treated with HIV env peptide V3-loop Despite the results presented immediately above, the location of R15K (SEQ ID NO:1) in a variable region (V3-loop) of HIV gp160 could be viewed as a reason for not selecting this peptide as a potential vaccine candidate. However, a comparison of gp160 amino acid sequences from 245 different HIV isolates has shown that as little as five different consensus sequences can be defined on a serological basis among all the viral isolates (LaRosa et al., 1990). Therefore, the inventors propose that a cocktail of CTL-inducing peptides from V3-loop regions encompassing all the principal HIV groups (which may be five or less) may be sufficient for generating CTLs specific for cells expressing gp120 from most if not all HIV strains. Such a mixture would then serve as a prototype vaccine for evaluation for prevention of HIV infection of humans.

EXAMPLE 6

Enhancement of Virus-Specific CTL Responses by T helper Cell-Inducing Peptides

The present example concerns a method for enhancing the systemic distribution, level of activity, and longevity of virus-specific CTLs induced in response to CTL epitope-bearing peptides. This method involves the addition of a separate and distinct class of peptides to the immunization mixture that possess T helper cell-inducing activity as a means to enhance the CTL-inducing capacity of a given peptide immunogen.

The inventors method for inducing CTL responses against peptide immunogens, as described in Example 5, results in rapid CTL induction in the proximal lymph node (near the site of injection). However, it was noted that distant lymphoid tissue (i.e. spleen) accumulated a lower level of antigen-specific CTLs. The inventors next reasoned that the further induction of T helper cell activity may be advantageous in improving the dissemination of specific CTLs. As the method described above allows screening of CTL-inducing peptides without the need to include T helper epitope sequences, the inventors tested whether HIV T-cell helper peptides physically mixed with the HIV-specific CTL-inducing peptide (RIQRGPGRAFVTIGK, R15K, seq id no:1) would enhance the observed CTL response in mice following multiple subcutaneous (sc) injections. The T helper peptide selected for these studies was CRIKQIINMWQGVGKAMYA, C19A, (seq id no:2), which had been previously demonstrated to have T helper cell-inducing activity.

Balb/c mice were injected sc three times at bi-weekly intervals with R15K (seq id no:1) peptide mixed with the T helper peptide prepared in one of three forms: monomer, lipid tailed and di-sulphide polymer. One week after the last injection, spleen cells were obtained, restimulated and tested for CTL activity. This experiment was successful and significant CTL activity was observed in all the mice (Table 8). This experiment was subsequently repeated by injecting mice so with a mixture of R15K (SEQ ID NO:1) and the monomeric form of the T helper peptide. In this experiment, spleen cells were assayed for HIV-specific CTL response after one, two and three sc injections and a lower, but significant, level of positive CTL responses were observed (Table 9).

TABLE 8

CTL Activity of Spleen Cells From Balb/c Mice Immunized Subcutaneously (sc) with a Mixture of R15K (seq no:1) and the T-Helper Cell peptide C19A (seq id no:2)

| | | % specific Lysis at various E:T$^a$ ratios | | | |
|---|---|---|---|---|---|
| Immunogen | Target cells | 200:1 | 100:1 | 50:1 | 25:1 |
| R15K + 122$^b$ | p815$^e$ | 22.9 | 12.5 | 7.9 | 5.1 |
| | p815 + R15K$^f$ | 53.6 | 47.4 | 34.0 | 25.2 |
| | p815 + 122$^g$ | 10.6 | 5.4 | 3.8 | 1.3 |
| R15K + 65$^c$ | p815 | 8.4 | 13.4 | 7.5 | 4.4 |
| | p815 + R15K | 48.4 | 27.9 | 25.3 | 12.9 |
| | p815 + 122 | 6.8 | 9.9 | 0 | 0 |
| R15K + 66$^d$ | p815 | 27.4 | 16.0 | 16.0 | 10.5 |
| | p815 + R15K | 58.8 | 37.4 | 33.8 | 20.7 |
| | p815 + 122 | 16.3 | 7.0 | 4.1 | 2.2 |

$^a$ = Effector to target cell ratios
$^b$ = T = Helper cell peptide in its monomeric form mixed with R15K
$^c$ = T-Helper cell peptide in its polymeric form mixed with R15K
$^d$ = T-Helper cell peptide in its lipid = tailed from mixed with R15K
$^e$ = MHC-matched target cells (P815, H-2$^d$)
$^f$ = P815 target cells pre-incubated with R15K
$^g$ = P815 target cells pre-incubated with monomeric form of T-helper cell peptide.

Mice were immunized subcutaneously with the peptide mixture emulsified in complete Freund's adjuvant (1:1) at bi-weekly intervals for six weeks (total 3 injections). Spleens were harvested one week after the last injection and restimulated for 5 days, as described by Sastry et al., 1992. Peptide 122 is a T-helper cell stimulating peptide that has the sequence CRIKQIINMWQGVGKAMYA, also herein referred to as C19A (seq id no:2); R15K is a CTL-inducing peptide that has the sequence RIQRGPGRAFVTIGK (seq id no: 1). Both sequences originated from the gp120 sequence of HIV-1 (Sastry et al., 1991; 1992).

TABLE 9

CTL Activity of Spleen Cells from Balb/c Mice Immunized Subcutaneously (sc) with a Mixture of R15K (seq id no:1) and the T-Helper Cell peptide C19A (seq id no:2)

| | | % specific Lysis at various E:T$^a$ ratios | | | |
|---|---|---|---|---|---|
| # of Injections | Target cells | 100:1 | 50:1 | 25:1 | 12.5:1 |
| 1 | p815$^c$ | 2.9 | 4.7 | 3.3 | 3.3 |
| | p815 + R15K$^d$ | 11.0 | 7.7 | 3.6 | 0.1 |
| | P815 + 122$^e$ | 9.4 | 3.8 | 2.2 | 1.6 |
| 2 | p815 | 5.5 | 3.8 | 1.6 | 1.8 |
| | p815 + R15K | 13.1 | 11.0 | 5.0 | 0.8 |
| | p815 + 122 | 3.0 | 4.3 | 2.8 | 1.8 |
| 3 | p815 | 6.6 | 3.6 | 4.3 | 4.3 |
| | p815 + R15K | 13.7 | 4.3 | 5.6 | 0.5 |
| | p815 + 122 | 10.5 | 5.2 | 4.9 | 6.8 |

$^a$ = Effector to target cell ratios
$^b$ = Mice were immunized either once, twice or three times with a mixture of R15K (SEQ ID NO:1) and the monomeric form of T-helper cell peptide
$^c$ = MHC-matched target cells (P815, H-s$^d$)
$^d$ = P815 target cells pre-incubated with R15K (SEQ ID NO:1)
$^e$ = P815 target cells preincubated with the monomeric form of T-helper cell peptide Mice were immunized subcutaneously with the peptide mixture emulsified in CFA (1:1) at two week intervals. One week after each injection, spleen cells were harvested and restimulated as described by Sastry et la., 1992.

Figure 4A:
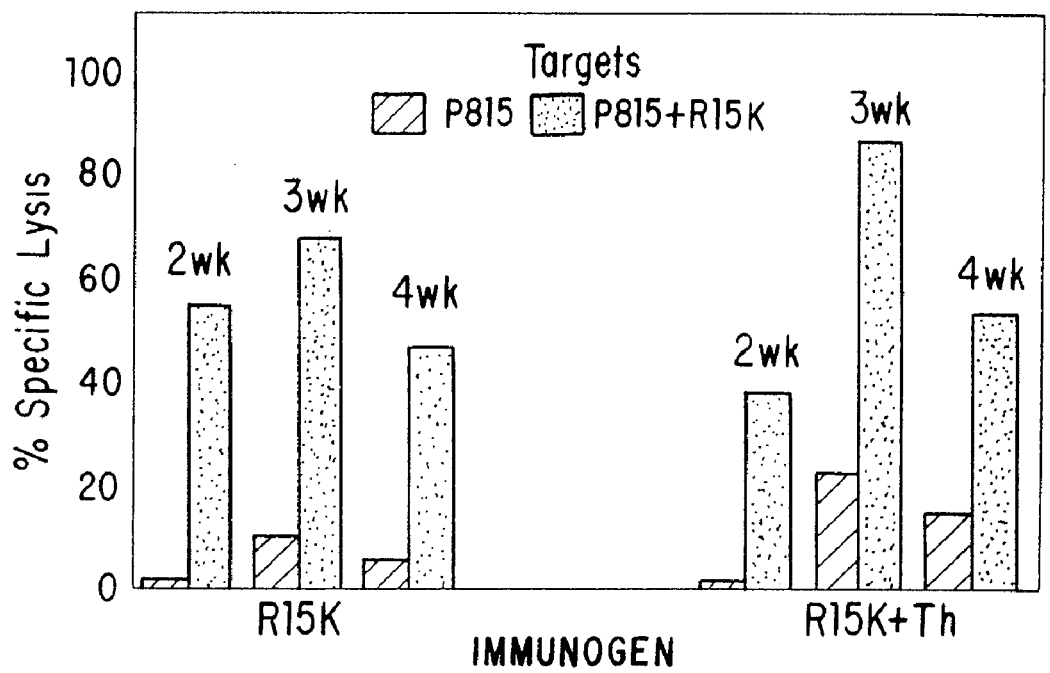
FIG. 4. CTL activity of spleen cells from ice immunized with R15K/R15K+Th. 6-8 week old Balb/c mice were immunized in hind footpad with 100 μg of R15K peptide (SEQ ID NO:1) alone or 100·g of a helper T-cell peptide (T$_h$) emulsified in CFA. At 2, 3 or 4 weeks post-immunization, both PLN and spleen cells from the mice were collected and restimulated for 5 days with irradiated syngeneic mouse spleen cells pretreated with R15K (SEQ ID NO:1) for 2 hours. A standard 4 hour $^{51}$Cr-release assay was performed, as described by Sastry et al. (1992). Representative data from PLN (A) and spleen cells (B) are shown, and demonstrate that a helper T-cell peptide from the HIV env protein enhances the systemic CTL response to RISK V3 loop peptide (seq id no:1).

To date the R15K (SEQ ID NO:1) peptide by itself has not been shown by any other group to be capable of inducing a CTL response. But the present inventors, as disclosed herein, have demonstrated CTL induction in the popliteal lymph node within 7 days by a single id immunization of Balb/c mice with R15K (SEQ ID NO:1) alone (FIG. 4A). It was therefore reasoned that a mixture consisting of R15K (SEQ ID NO:1) and the T helper peptide when injected once by the id route might be sufficient to achieve systemic spread and longevity of HIV-specific CTL response.

Figure 4B:
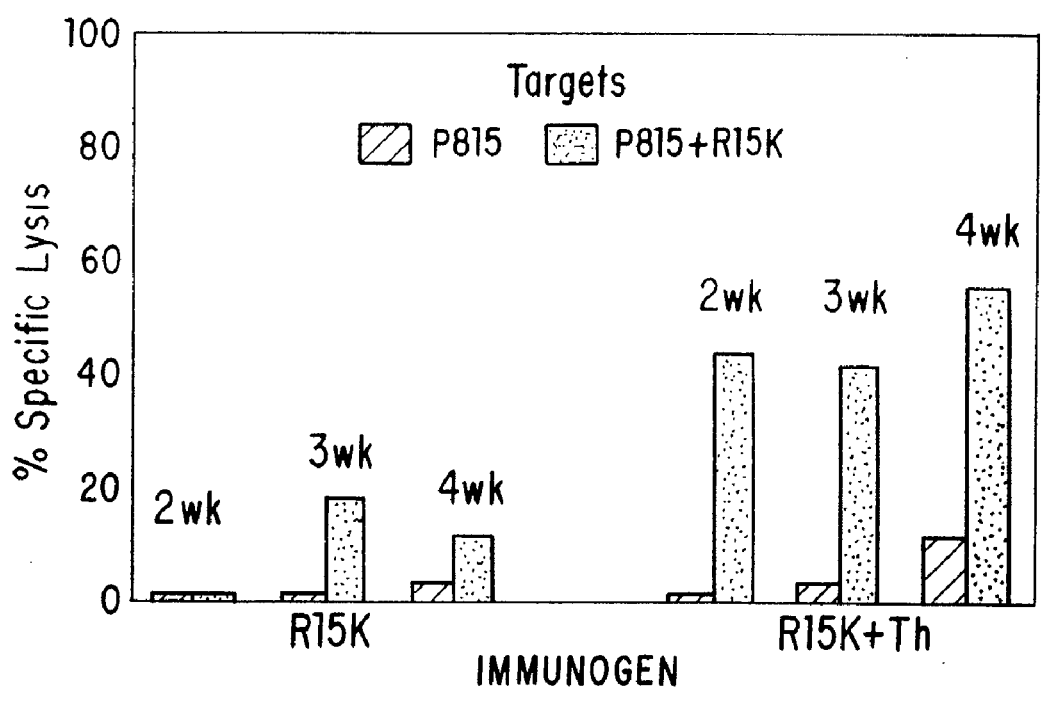

A number of mice were immunized with a single id injection in the footpads with either the CTL peptide (R15K, SEQ ID NO:1) alone or in a mixture with the T helper peptide C19A (seq id no:2). The results (FIG. 4) showed that mice immunized with the mixture had substantially higher CTL responses in the spleen than mice receiving just the R15K (SEQ ID NO:1) peptide alone (FIG. 4B). In addition, the high level of CTL response in the spleen was maintained for up to eight weeks after a single id injection, whilst the helper T-cell peptide (C19A, seq id no:2) injected alone lacked CTL-inducing activity.

Lasarte et al. (1992) recently reported that multiple intraperitoneal injections of mixtures of an R15K-bearing CTL epitope and a helper T-cell epitope, KQIINMWQEVGKAMYA (SEQ ID NO:46), in mice induced a low level HIV-specific CTL response after three weeks. However, in these experiments, the CTL peptide by itself was not capable of inducing HIV-specific CTLs even after multiple injections. Therefore, the role of T helper peptide in these studies is not clear. On the other hand, the studies described above show that the CTL-peptide possesses the CTL-inducing capacity and the role of T helper peptide is to disseminate and enhance that inherent CTL response of the CTL-peptide.

These studies therefore indicate that in order to achieve an efficient, systemic and long lasting cell-mediated immunity, the candidate vaccine preparation should ideally include both T helper and CTL peptides. Another important aspect of this invention is that such a mixture given once intradermally is sufficient to induce a long lasting systemic antigen-specific CTL response.

EXAMPLE 7

Rapid Induction of Influenza Virus- and Sendai Virus-Specific CTLs

The protocol developed for the induction of HIV-specific CTLs, as described above in Example 5, was believed to be generally applicable to the identification, selection and assay of any peptide with unknown epitope specificity, for its ability to prime CTLs in vivo. Accordingly, the in vivo peptide-induction of CTLs specific for influenza virus was examined. Deres et al., (1989) had previously shown that a synthetic peptide R⁻, TYQRTRALVTG (aa 147-158 SEQ ID NO:8), corresponding to a portion of the nucleoprotein of influenza virus, could prime influenza virus-specific CTLs in mice in vivo only when covalently linked through the N-terminus to tripalmitoyl-S-glycerylcysteinyl-seryl-serine ($P_3CSS$). However, using the protocol described above, specific CD8⁺ CTLs, that lysed target cells pre-treated with this peptide, could be induced in vivo by immunization with the free synthetic peptide (Table 10).

Employing this immunization protocol, an in vivo CTL response was also successfully generated against the unmodified free synthetic peptide, HGEFAPGNYPAL-WSYA (SEQ ID NO:9), which represents the immunodominant CTL epitope from the nucleoprotein of Sendai virus (B105: NP 321-336).

Thus, this method was indeed found to be useful in systems other than those related to the HIV virus. Furthermore, it is believed that this rapid screening method will have medical utility for developing candidate vaccines and therapeutics for various infectious diseases.

TABLE 10

In Vivo Priming of Peptide Specific CTLs in Balb/C Mice with a Free Synthetic Peptide (B106) from Influenza Virus Nucleoprotein

| Treatment To Effector Cells | Target Cells | % Specific Lysis at Various E:T$^a$ Ratios | | | |
|---|---|---|---|---|---|
| | | 160:1 | 80:1 | 40:1 | 20:1 |
| No Treatment | P815$^b$ | 5.7 | 0 | 0 | 2.5 |
| No Treatment | P815 + B106$^c$ | 83.9 | 76.6 | 57.1 | 47.3 |
| No Treatment | P815 + B105$^d$ | 11.0 | 26.0 | 19.3 | 16.0 |
| + Complement | P815 + B106 | 83.3 | 73.6 | 58.2 | 39.7 |
| + anti-CD4 + C | P815 + B106 | 67.2 | 59.3 | 40.7 | 25.8 |
| + anti-CD8 + C | P815 + B106 | 2.5 | 0 | 0 | 0.4 |
| + anti-CD4 | P815 + B106 | 64.8 | 67.9 | 44.7 | 24.8 |
| + anti-CD8 | P815 + B106 | 53.6 | 43.3 | 23.7 | 5.8 |
| No Treatment | 3A9$^e$ | 0 | 0 | ND | ND |
| No Treatment | 3A9 + B106$^f$ | 0 | 0 | 0 | 0 |

ND = Not Done
$^a$ = E:T = Effector to target cell ratio
$^b$ = MHC-matched target cells (H-2$^d$)
$^c$ = H-2$^d$ target cells pre-treated with Influenza virus peptide
$^d$ = H-2$^d$ target cells pre-treated with Sendai virus peptide
$^e$ = MHC-mis-matched target cells (H-2$^k$)
$^f$ = H-2$^k$ target cells pre-treated with Influenza virus peptide

EXAMPLE 8

Inhibition of HIV-1 Infection and Syncytia Formation by Human Cells by Synthetic Peptides from gp120

The present example describes the identification and use of synthetic peptides, derived from gp120, to protect human cells against HIV-1 infection, and to inhibit syncytia formation. MT-4 cells are human T cells that are chronically infected by the human T cell leukemia virus type 1 and undergo lytic infection with HIV-1 (Larder et al., 1989). Therefore, inhibition of HIV-1 infection of MT-4 cells will prevent cell death.

Figure 5:
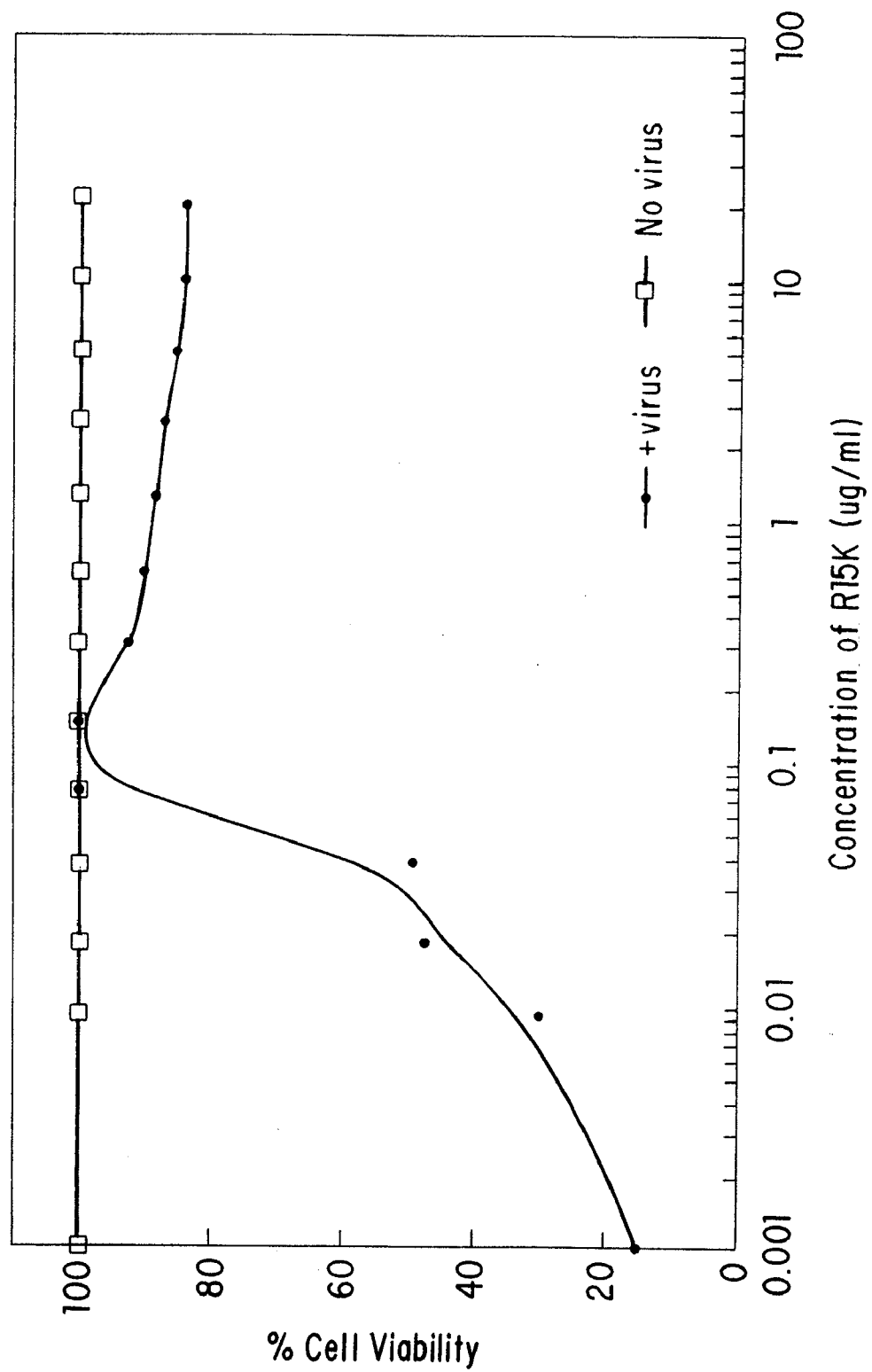
FIG. 5. Peptide RISK (SEQ ID NO:1) inhibits infection of human T cells (MT-4) by HIV-1. MT-4 cells are human T cells that are chronically infected by the human T cell leukemia virus type 1 and undergo lytic infection with HIV-1 (Larder et al., 1989). Therefore, inhibition of HIV-1 infection of MT-4 cells will prevent cell death. In these experiments, MT-4 cells (5×10$^4$/100 μl) were preincubated in triplicate wells of 96 well microtiter plates with various concentration of the R15K peptide for 15 minutes at 37·C, and challenged with HIV-1. Controls included cells alone and cells infected with HIV-1, but without added peptide. Seven days after infection, the total number of viable cells was determined using the MTT dye reduction assay of Larder et al. (1989). The line marked with no virus shows effect of various concentrations of peptide on the survival of MT4 cells in the absence of HIV-1 infection. The line marked with "+ virus" shows protective effect of peptide R15K (seq id no:1).
Figure 6:
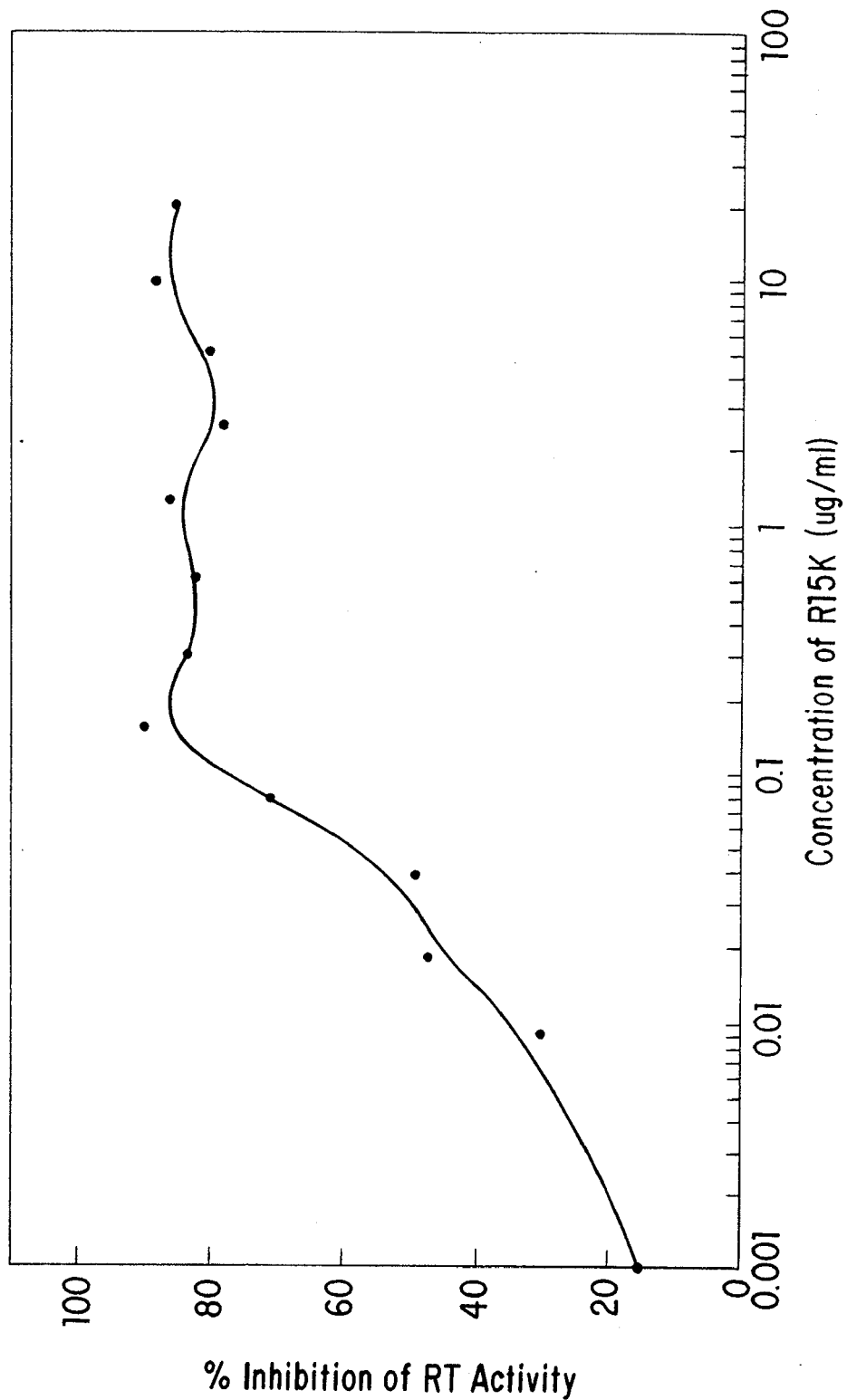
FIG. 6. Peptide R15K (SEQ ID NO:1) inhibits HIV-1 infection of MT-4 cells as measured by a reverse transcriptase assay. In these experiments MT-4 cells were infected as in FIG. 5, but instead of measuring the cytopathic effect, the amount of reverse transcriptase (RT) activity in the culture medium was determined seven days after infection by the method of Popovic et al. (1984).
Figure 7:
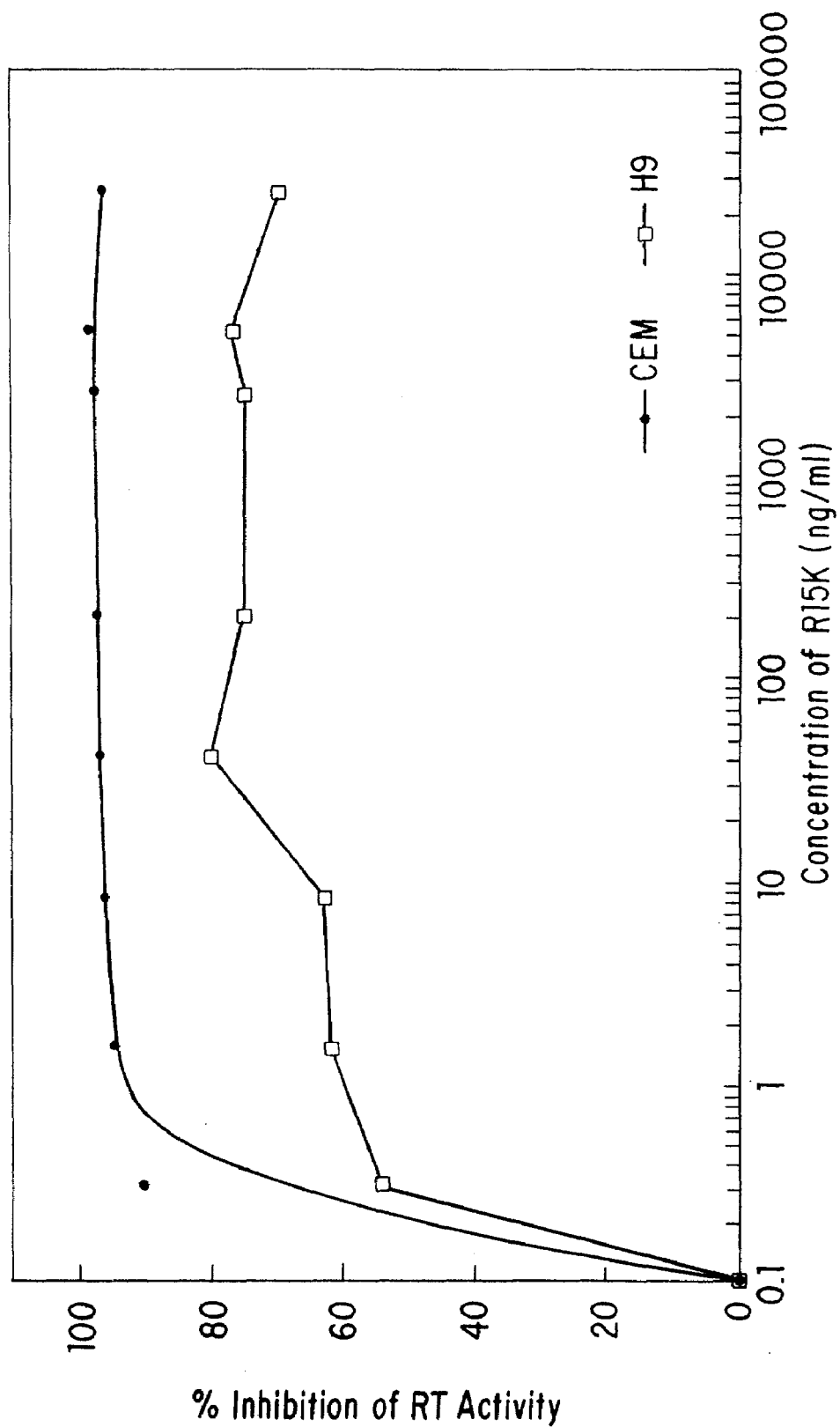
FIG. 7. Peptide RISK (SEQ ID NO:1) inhibits HIV-1 infection of human T cell lines CEM and H9. The CEM and H9 cells (1×10$^5$ cells/well) in separate experiments were infected with HIV-1 in triplicate wells of a 48 well plate in the presence or absence of various concentrations of peptide R15K (SEQ ID NO:1). The experimental protocol was as described in FIG. 5. Seven days after infection, reverse transcriptase (RT) activity in the culture supernatant was measured by the method of Popovic et al. (1984).

The ability of gp120 derived synthetic peptides to inhibit HIV infection of cells was investigated. Evidence was obtained to demonstrate that synthetic peptides of varying length (8-24) amino acids) selected from the V3 loop of gp120 inhibited HIV infection of both cultured human T cells (FIGS. 5, 6 & 7) as well as freshly prepared primary human T cells (FIG. 8).

Figure 8:
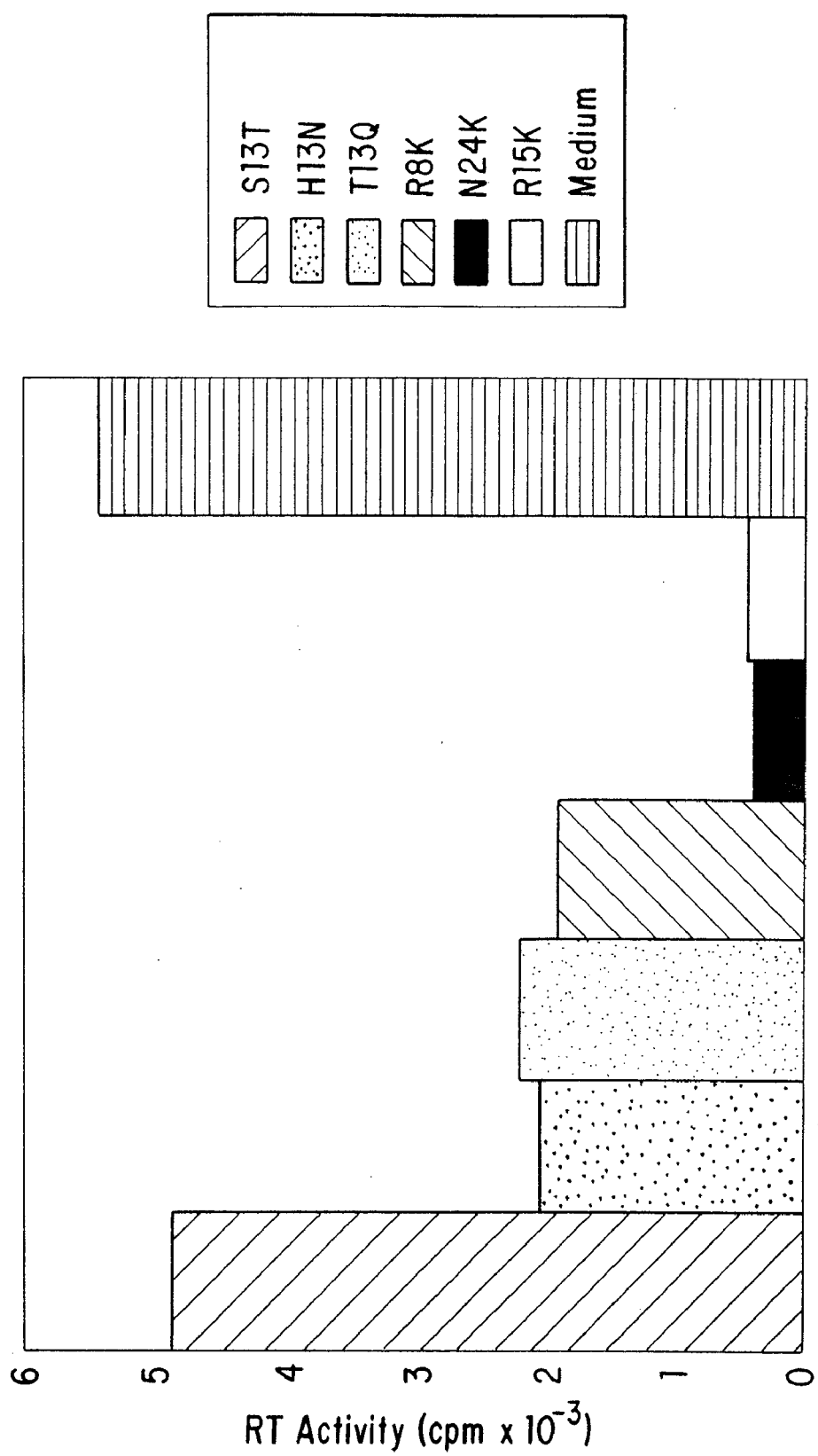
FIG. 8. V-3 loop peptides inhibit HIV-1 infection of primary human T cells. Peripheral blood mononuclear cells (PBMCs) from healthy HIV-1 seronegative donors were separated by Ficoll-hypaque centrifugation. E-rosetting was used for the preparation of T cell enriched lymphocyte population, as described by Mannhalter et al. (1986). T-cells (1×10$^6$/ml) were incubated in triplicate wells of 96 well microtiter plates with medium alone or control unrelated peptide (corresponding to a sequence in c-mos protooncogene product) or various V3 loop peptides at 1 μg/ml concentration. Other peptides are: H13N, V3-loop peptide from HIV-1mn strain (seq id no:7); T13Q, V3-loop peptide from V3-loop of HIV-1rf strain (seq id no:6); R8K, a 8 amino acid peptide from V3-loop of HIV-1 IIIB strain (seq id no:5); N24G, a 24 amino acid peptide for HIV-1 IIIB V3-loop (seq id no:3); and R15K, a 15 amino acid peptide for HIV-1 IIIB V3-loop (seq id no:1). After 9 days, reverse transcriptase activity in culture supernatant was determined according to the method of Popovic et al. (1984).

It was observed that both the 24 amino acid peptide N24G (aa 308-311, NNTRKSIRIQRGPGRAFVTIGKIG, seq id no:3) and the 15 amino acid peptide R15K (aa 315-329, RIQRGPGRAFVTIGK, seq id no:1), with sequences derived from the V3 loop of HIV-1 IIIB, inhibited HIV-1 infection of primary human T cells by 92% at 1 µg/ml (approximately 0.4-0.6 µM) concentration (FIG. 8). An 8 amino acid shorter form of the V3 loop peptide, R8K (aa 322-329, RAFVTIGK, seq id no:5) also showed 66% inhibition of HIV-1 infection of primary human T cells at 1 µg/ml (approximately 1.25 µM) concentration (FIG. 8). Synthetic peptides from V3 loop regions of heterologous isolates, HIV-1mn (T13Q, TKGPGRVIYATGQ, seq id no:6) and HIV-1rf (H13N, HIGPGRAFYTTKN, seq id no:7), also showed significant inhibition (>60%), each at 1 µg/ml (approximately 0.78 µM) concentration, of cells by the IIIB strain (FIG. 8).

A variety of other peptides with sequences derived from the V3 loops of other HIV-1 strains were also found to exhibit significant activity with respect to the inhibition of HIV-1 IIIB infection of human cells. As detailed in Table 11A (SEQ ID NOS:11 through 14, 18, 23, 25 through 27 and 1, respectively), these peptides include D23 (SEQ ID NO:11), D24 (SEQ ID NO:12), D25 (SEQ ID NO:13), D26 (SEQ ID NO:14), D30 (SEQ ID NO:18), D35 (SEQ ID NO:23), D38 (SEQ ID NO:25), D39 (SEQ ID NO:26), D40 (SEQ ID NO:27) and D$$ (SEQ ID NO:1) which reflect a variety of strains such as mn, rf, wmj-3, sc, z6, eli, mn (y-1) and mn (y-p). However, it is important to note that this assay was confined specifically to inhibiting the infection of the heterologous strain HIV-1 IIIB. Therefore peptides, such as those in Table 11B (SEQ ID NOS:15 through 22 and 24, respectively), which did not show activity in this specific assay may still have utility as infection-inhibiting sequences to combat the variety of HIV strains known to be present in the infected human population.

TABLE 11A

EFFECT OF V3 LOOP PEPTIDES ON HIV-1 IIIB INFECTION OF HUMAN CELLS

| PEPTIDE NO. | STRAIN | SEQUENCE | RT ACTIVITY (CPM) | % RT INHIBITION |
|---|---|---|---|---|
| D23(24aa) | MN | YNKRKRIHIGPGRAFYTTKNNIGC | 94 | 98.8 |
| D24(15aa) | MN | RIHIGPGRAFYTTKN | 5000 | 22.1 |
| D25(15aa) | WMJ-3 | SLSIGPGRAPRTREI | 4342 | 42.4 |
| D26(24aa) | RF | NNTRKSITKGPGRVIYATGQIIGD | 2093 | 72.2 |
| D30(15aa) | SC | SIHIGPGRAFYATGD | 3443 | 54.3 |
| D35(15aa) | Z62 | STPIGLGQALYTTRG | 5242 | 30.3 |
| D38(15aa) | ELI | RTPTGLGQSLYTTRS | 5823 | 33.7 |
| D39(15aa) | MN(Y-L) | RIHIGPGARFLTTKN | 1978 | 73.8 |
| D40(15aa) | MN(Y-F) | RIHIGPGRAFFTTKN | 2805 | 62.8 |
| D44(15aa) R15K | IIIB | RIQRGPGRAFVTIGK | 2021 | 73.2 |
| Uninfected cells | | | 558 | — |

TABLE 11B

EFFECT OF V3 LOOP PEPTIDES ON HIV-1 IIIB INFECTION OF HUMAN CELLS

| PEPTIDE NO. | STRAIN | SEQUENCE | RT ACTIVITY (CPM) | % RT INHIBITION |
|---|---|---|---|---|
| D27(15aa) | NY-5 | GIAIGPGRTLYAREK | 7657 | 0 |
| D28(15aa) | RF | SITKGPGRVIYATGQ | 7634 | 0 |
| D29(15aa) | CDC4 | RVTLGPGRVWYTTGE | 13009 | 0 |
| D31(15aa) | Z3 | SIRIGPGKVFTAKGG | 11877 | 0 |
| D32(15aa) | SF2 | SIYIGPGRAFHTTGR | 8002 | 0 |
| D33(15aa) | MAL | GIHFGPGQALYTTGI | 8959 | 0 |
| D34(15aa) | Z321 | SISIGPGRAFFATTD | 11142 | 0 |
| D37(15aa) | JY1 | STPIGLGQALYTTRI | 7027 | 0 |
| No Peptide | | | 7528 | 0 |
| Uninfected cells | | | 558 | — |

The peptides in this table are represented by SEQ ID NOS:11 through 14, 18, 23, 25 through 27, 1, 15 through 22 and 24, respectively.

Figure 10:
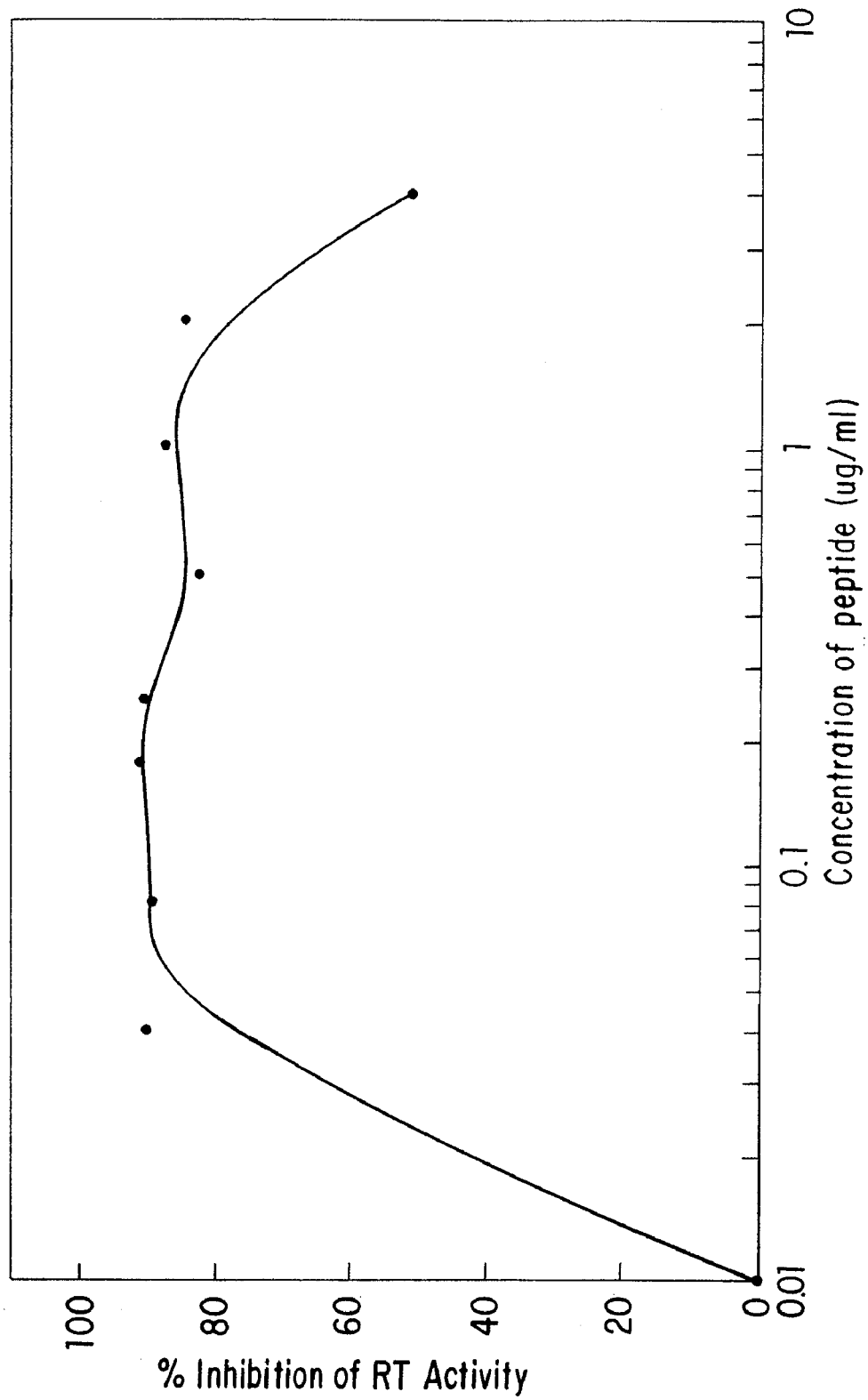
FIG. 10. Peptide E13V (seq id no:4) from the amino terminal domain of gp120 inhibits HIV-1 infection of primary human T-cells. Experimental details are same as in FIG. 8 except that in this experiment, different concentrations of peptide E13V (SEQ ID NO:4) was used in place of R15K (SEQ ID NO:1).

The capacity of peptide E13V, EQLWVTVYYGVPV (seq id no:4), from the amino-terminal portion of gp120 to inhibit HIV-1 infection of primary human T cells was also determined. It was observed that this peptide, at as low as 1 ng/ml concentration (approximately 0.77 nM), inhibited HIV-1 infection by 90% (FIG. 10).

Further studies were conducted to determine the effect of V3 loop synthetic peptides from different HIV-1 strains on syncytium formation. For these studies HeLa CD4 cells were infected with recombinant vaccinia viruses expressing the envelope protein gp160 of HIV-1 IIIB, mn or rf strains, at an m.o.i. of 100, in the presence and absence of V3 loop peptides from respective the HIV-1 stains (i.e., R15K, $H_{13}N$ and T13Q) (SEQ ID NOS:1, 7 and 6, respectively). At 18 hours post infection, cells were observed under microscope, using a magnification of 100, for syncytia.

In these studies, no syncytia were observed in cells incubated with the synthetic peptides before infection with the respective recombinant vaccinia viruses. These results clearly demonstrate the capacity of the V3 loop peptides to inhibit cell to cell spread of HIV-1.

Figure 9:
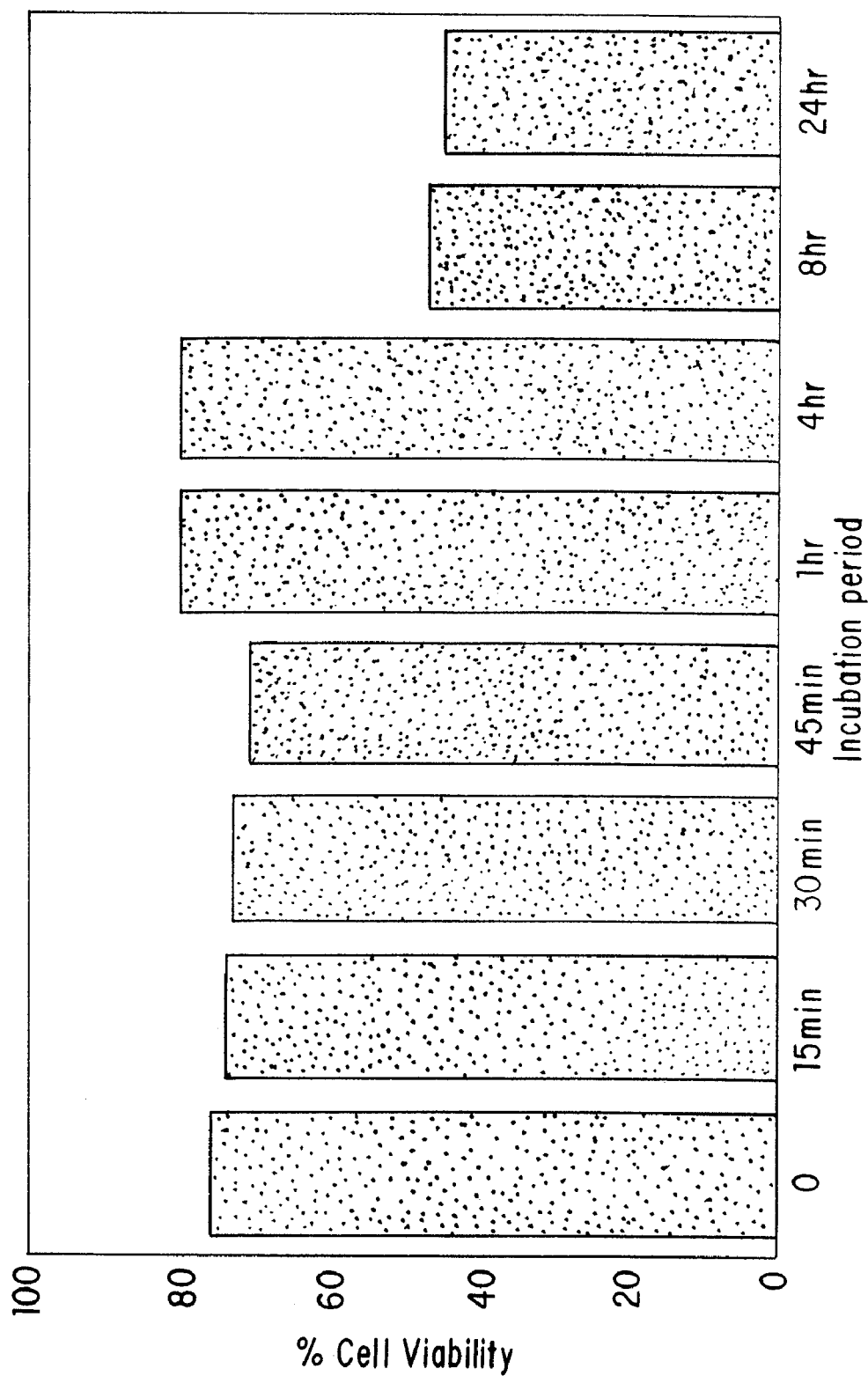
FIG. 9. Serum stability of peptide R15K: The R15K peptide (seq id no:1) was incubated at 37·C with fetal bovine serum at 100 μg/ml concentration for 24 hours. At different time intervals aliquots of peptide/serum mixture corresponding to 1 μg/ml final concentration were added to MT-4 cells in a 96 well microtiter plate. After 15 minutes of incubation with peptide, MT-4 cells were infected with HIV-1 as described in FIG. 5. Seven days after infection, the total number of viable cells was determined by the MTT-dye reduction assay (Larder et al., 1989). The controls included cells incubated in medium alone with and without virus infection and cells infected with virus and incubated with R15K (SEQ ID NO:1) peptide that was not pre-incubated in fetal calf serum.

Studies were conducted to examine the stability of the R15K peptide from HIV-1 IIIB isolate in serum. In these studies the R15K (seq id no:1) peptide was incubated in fetal calf serum at 37·C and at different time intervals during the incubation aliquots at a final concentration of 1 µg/ml (approximately 0.6 µM) were tested for inhibition of HIV-1 infection of a human T cell line (MT-4 cells). The results are shown in FIG. 9. The R15K (SEQ ID NO:1) peptide retained its full strength inhibitory activity for up to 4 hours and 50% of control untreated peptide inhibitory activity was retained even after 24 hours incubation at 37·C in fetal calf serum.

It is envisioned that stability examinations will be conducted on any synthetic peptide, or mixtures thereof, identified for potential clinical use. Such tests will include, for example, pre-incubation in human serum and plasma; treatment with various proteases; and also temperature- and pH-stability analyses. If found to be necessary, the stability of the synthetic peptides may be enhanced by any one of a variety of methods such as, for example, employing d-amino acids in place of 1-amino acids for peptide synthesis; using blocking groups like t-boc and the like; or encapsulating the peptides within liposomes. The bio-availability of select mixtures of peptides may also be determined by injecting radio-labelled peptides into mice and rhesus monkeys and subsequently analyzing their tissue distribution.

In addition to the inventors' previous demonstration that the R15K (SEQ ID NO:1) peptide can induce CTL responses (see above, Example 5), they also show this peptide and its analogues from other HIV-1 isolates, to efficiently protect human T cells from HIV-1 infection. This activity was demonstrated using cultured cells such as H9, CEM and MT-4 cells, and freshly prepared human T cells. These results indicate that the V3 loop peptides can act in two separate ways: 1) to induce HIV-1 specific cytotoxic T lymphocytes that specifically kill cells expressing HIV-1 gp120; and 2) to prevent infection of normal cells by infectious virus. Thus, these V3 loop peptides have utility not only for vaccines but also as therapeutic reagents to prevent HIV-1 infection in humans or reduce the spread of virus infection in HIV-infected individuals.

EXAMPLE 9

Induction of HIV-Specific T Cell Responses in Monkeys on Immunization with a Synthetic Peptide Cocktail The present example describes the successful induction of HIV-specific T cell responses in rhesus monkeys with a mixture of eight synthetic peptides, seven of which were derived from conserved regions of the HIV-1 envelope protein. These results, demonstrating the induction of HIV-1 specific T cell responses in a non-human primate model, constitute an important step towards identifying and formulating a synthetic peptide-based vaccine that can induce a broad based cell-mediated immunity for protecting humans against HIV infection.

In the present studies, three rhesus monkeys (#7, #23 and #283C) were immunized subcutaneously with 1 ml (0.1 ml/site) of a mixture of eight synthetic peptides (300·g of each peptide in sterile water) emulsified in complete Freund's adjuvant at 1:1 ratio. These eight peptides, termed 61 (SEQ ID NO:42), 63 (SEQ ID NO:43), 104 (SEQ ID NO:28), 105 (SEQ ID NO:29), 111 (SEQ ID NO:35), 113 (SEQ ID NO:37), 116 (SEQ ID NO:40) and R15K (SEQ ID NO:1) (Table 12), had previously been identified as gp160-specific T cell active synthetic peptides. At 3 and 7 weeks after the primary immunization, two booster injections of the peptide mixture (150·g of each peptide in sterile water) emulsified in incomplete Freund's adjuvant were given to each monkey. Monkey #7 was terminated after 34 weeks, for health reasons unrelated to the study, while the remaining two monkeys (#283C and #23) received one additional booster injection at 25 weeks.

TABLE 12

AMINO ACID SEQUENCES OF IMMUNIZING PEPTIDES

| peptide 61 | aa586-598 | YLRDQQLLGIWGC |
| peptide 63 | aa519-543 | FLGFLGAAGSTMGAASLTLTVQARC |
| peptide 104 | aa45-55 | VYYGVPVWKEA |
| peptide 105 | aa48-61 | GVPVWKEATTLFC |
| peptide 111 | aa118-130 | LWDQSLKPCVKLT |
| peptide 113 | aa204-216 | SVITQACSKVSFE |
| peptide 116 | aa240-252 | GTGPCTNVSTVQC |
| peptide R15K | aa315-329 | RIQRGPGRAFVTIGK |

The numbering of amino-and carboxy terminal amino acids of each peptide are according to the sequence reported by Modrow et al., 1987. The peptides in this table are represented by SEQ ID NOS:42, 43, 28, 29, 35, 37, 40 and 1, respectively.

At two week intervals following the first immunization of each animal, 15 ml of whole heparinized blood was collected by venous puncture. The peripheral blood mononuclear cells (PBMC) were separated by standard ficoll-hypaque centrifugation and employed in proliferation assays. The PBMCs were monitored every two weeks for a period of 32 weeks for proliferative responses against individual peptides and recombinant gp160.

It was found that PBMCs from all three rhesus monkeys showed good proliferative responses with peptides 104 (aa 45-55; SEQ ID NO:28), 111 (aa 118-130; SEQ ID NO:35) and 63 (aa 519-543; SEQ ID NO:43); while weak responses were observed with peptides 113 (aa 204-216; SEQ ID NO:37) and 116 (aa 240-252; SEQ ID NO:40) (Table 13). Two of the three rhesus monkey-derived PBMC preparations also showed good proliferative responses with peptide 61 (aa 586-598; SEQ ID NO:42) (Table 13). A significant response was not detected in any of the monkeys with peptides 105 (aa 48-61; SEQ ID NO:29) and R15K (aa 315-329; SEQ ID NO:1). PBMCs from all three monkeys showed significantly high proliferative responses with recombinant gp160, the HIV-1 envelope protein precursor, for the entire period of the experiment.

TABLE 13

T-cell Proliferation Responses

| | Rhesus Monkey | | |
|---|---|---|---|
| Peptide | #7 | #23 | #283C |
| 104 (aa45-55) | 4+ | 2+ | 4+ |
| 111 (aa118-130) | 3+ | 2+ | 3+ |
| 63 (aa519-543) | 2+ | 4+ | 3+ |
| 113 (aa204-216) | 1+ | 2+ | 2+ |
| 116 (aa240-252) | 1+ | 3+ | 2+ |
| 61 (aa586-598) | — | 3+ | 2+ |
| R15K (aa315-329) | — | — | — |
| GP160 (aa1-863) | 6+ | 4+ | 4+ |

(—), no detectable response; (1+), poor response; (2+), good response; (3+), better response; (4+, 6+), best response.
The peptides in this table are represented by SEQ ID NOS:28, 35, 43, 37, 40, 42 and 1.

These results demonstrate that mixtures of synthetic peptides from HIV env gene product can prime gp160-specific T cell responses in rhesus monkeys. Because of their ability to induce specific T-cell responses both in mice and rhesus monkeys, these HIV env peptides are proposed to be useful as components of vaccines to prevent HIV infection in humans.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for directly inhibiting HIV entry into a cell comprising the step of contacting said cell with an effective amount of a composition comprising a peptide of 8 to 24 residues comprising the sequence RAFVTIGK (SEQ ID NO:5), wherein said cell is in a human subject.

2. The method of claim 1, wherein said peptide is 8 residues in length.

3. The method of claim 1, wherein said peptide is 15 residues in length.

4. The method of claim 3, wherein said peptide comprises the sequence RIQRGPGRAFVTIGK (SEQ ID NO:1).

5. The method of claim 1, wherein said peptide is 24 amino acids in length.

6. The method of claim 5, wherein said peptide comprises the sequence NNTRKSIRIQRGPGRAFVTIGKIG (SEQ ID NO:3).

7. The method of claim 1, wherein said peptide is in the form of a multimer.

8. The method of claim 1, wherein said composition is dispersed in a pharmaceutically acceptable aqueous medium.

9. The method of claim 1, wherein said composition is administered at a dosage range of between about 10 micrograms to about 500 milligrams.

10. The method of claim 9, wherein dosage range is about 50 micrograms to about 1 milligram.

11. The method of claim 9, wherein said dosage range is about 100 micrograms.

12. The method of claim 1, further comprising contacting said cell with said composition a second time.

13. The method of claim 1, wherein said contacting comprises injection of said composition.

14. A method for directly inhibiting HIV entry into a cell in vitro comprising the step of contacting said cell with a composition comprising a peptide of 8 to 24 residues comprising the sequence RAFVTIGK (SEQ ID NO:5).

* * * * *